(12) United States Patent
Cash et al.

(10) Patent No.: US 6,602,994 B1
(45) Date of Patent: Aug. 5, 2003

(54) DERIVATIZED MICROFIBRILLAR POLYSACCHARIDE

(75) Inventors: Mary Jean Cash, Wilmington, DE (US); Anita N. Chan, Wilmington, DE (US); Herbert Thompson Conner, Landenberg, PA (US); Patrick Joseph Cowan, Hockessin, DE (US); Robert Alan Gelman, Newark, DE (US); Kate Marritt Lusvardi, Chadds Ford, PA (US); Samuel Anthony Thompson, Wilmington, DE (US); Frank Peine Tise, Wilmington, DE (US)

(73) Assignee: Hercules Incorporated, Wilmington, DE (US)

( * ) Notice: Subject to any disclaimer, the term of this patent is extended or adjusted under 35 U.S.C. 154(b) by 0 days.

(21) Appl. No.: 09/248,246

(22) Filed: Feb. 10, 1999

(51) Int. Cl.[7] .................. C08B 11/00; C08B 11/193; C08B 11/08; C08B 11/12; B01J 13/00
(52) U.S. Cl. .................. 536/30; 536/43; 536/44; 536/84; 536/90; 536/91; 536/92; 536/95; 536/96; 536/97; 536/99; 536/100
(58) Field of Search ............... 536/30, 43, 44, 536/84, 90, 91, 92, 95, 96, 97, 99, 100

(56) References Cited

U.S. PATENT DOCUMENTS

| | | | |
|---|---|---|---|
| 3,418,133 A | | 12/1968 | Nijhoff |
| 3,676,423 A | * | 7/1972 | Elizer |
| 4,025,472 A | * | 5/1977 | Lepoutre |
| 4,341,807 A | | 7/1982 | Turbak et al. ............ 426/570 |
| 4,374,702 A | | 2/1983 | Turbak et al. ............ 162/100 |
| 4,378,381 A | | 3/1983 | Turbak et al. ............ 426/570 |
| 4,452,721 A | | 6/1984 | Turbak et al. ............ 252/310 |
| 4,452,722 A | | 6/1984 | Turbak et al. ............ 252/311 |
| 4,464,287 A | | 8/1984 | Turbak et al. ............ 252/312 |
| 4,481,076 A | | 11/1984 | Herrick ................ 162/158 |

(List continued on next page.)

FOREIGN PATENT DOCUMENTS

| | | |
|---|---|---|
| EP | 0 845 495 A2 | 11/1997 |
| EP | 0845495 | 6/1998 |
| EP | 0859011 | 8/1998 |
| JP | 59-84938 | 5/1984 |
| JP | 98-95803 | 4/1998 |
| JP | 10165823 | 6/1998 |
| WO | WO98/02486 | 1/1998 |
| WO | WO98/02487 | 1/1998 |
| WO | WO98/02499 | 1/1998 |
| WO | WO9938892 | 8/1999 |
| WO | 00 47628 | 8/2000 |

OTHER PUBLICATIONS

Cash et al., U.S. patent application Ser. No. 09/522,032, filed Mar. 9, 2000.
H. Yokota, J. Polmer Sci., Part C, 24, 423–425 (1986).
C.H. Haigler, Cellulose Chemistry and Its Applications, Nevell, pp 30–83, (1985).
N. Morss, J. Ogg, "Some Special Characteristics of Cellulose Ethers", SCI Monograph, 1966, Vol 24, pp 46–56.

(List continued on next page.)

*Primary Examiner*—James O. Wilson
*Assistant Examiner*—Everett White
(74) *Attorney, Agent, or Firm*—David Edwards

(57) ABSTRACT

A method for producing derivatized microfibrillar polysaccharide, including but not limited to cellulose, derivatized by steric and/or electrostatic forces, where the electrostatic forces are provided by anionic charge or by a combination of both anionic and cationic charge, by stabilizing and/or microfibrillating a polysaccharide starting material. A method of modifying the rheological properties of a composition of matter using derivatized microfibrillar polysaccharide. Method of improving coatings, paper manufacture, and the stability of emulsions, dispersions, and foams using a derivatized microfibrillar polysaccharide. Compositions that include derivatized microfibrillar polysaccharide, including paper compositions, comestible compositions, non-comestible spreadable compositions, and emulsions, dispersion, and foams.

40 Claims, 9 Drawing Sheets

U.S. PATENT DOCUMENTS

| | | | |
|---|---|---|---|
| 4,481,077 A | 11/1984 | Herrick | 162/158 |
| 4,483,743 A | 11/1984 | Turbak et al. | 162/100 |
| 4,487,634 A | 12/1984 | Turbak et al. | 106/203 |
| 4,500,546 A | 2/1985 | Turbak et al. | 514/781 |
| 4,676,904 A | 6/1987 | Schröder | 210/504 |
| 5,278,304 A * | 1/1994 | Kniewske et al. | |
| 5,374,444 A | 12/1994 | Langner | 426/590 |
| 5,588,861 A | 12/1996 | Townsend | 439/342 |
| 5,964,983 A | 10/1999 | Dinand et al. | 162/27 |
| 6,103,790 A | 8/2000 | Cavaille et al. | 524/13 |

OTHER PUBLICATIONS

M. Dolz, J. Bugaj., J. Pellicer, M.J. Hernandez, M. Gorecki, J. Pharm. Sci. 1997, vol. 86, pp 1283–1287.

M. Dolz, C. Roldan, J.V. Herraez, R. Belda, P. Sobrino, J. Dispersion Sci. and Tech., vol. 13 pp 95–113, 1992.

G. Regdon, I. Eros, Acta Pharm. Hung. 1988, vol. 58, pp 173–180 Chemical Abstracts 109:176212.

G. Regdon, I. Eros, Acta Pharm. Hung. 1988 vol. 58, pp 193–200 Chemical Abstracts 110:28967.

I. Eros, A. Mednyanszky, G. Regdon, Acta Pharm. Hung. 1986, vol. 56, pp. 273–282 Chemical Abstracts 106:90079.

G. Regdon, I. Eros, Acta Pharm. Hung. 1985 vol. 55, pp 68–75 Chemical Abstracts 103:59168.

J.A. Walecka, TAPPI, vol. 39, pp 458–463, 1956.

M. Nishiyama, J. Hosokawa, K. Yoshihara, T. Kubo, H. Kabeya, T. Endo, Trans. of Materials Soc., 1994, vol. 18A, pp 459–462.

B. Riedel et al., "Novel Polyanion–Polycation–Microfibride Blend Nonwovens Based on Cellulose Derivatives", Chemical Fibers International, vol. 49, No. 1, Mar., 1999, pp. 55–57.

* cited by examiner

DERIVATIZED MICROFIBRILLAR POLYSACCHARIDE

FIELD OF THE INVENTION

The present invention relates to derivatized microfibrillar polysaccharide. More specifically, the present invention relates to microfibrillar polysaccharide stabilized by steric and/or electrostatic forces, where the electrostatic forces are provided by anionic charge, or by a combination of both anionic and cationic charge.

BACKGROUND OF THE INVENTION

Polysaccharides are often found in nature in forms having fibrous morphology. Polysaccharides which are not found in nature in fibrous form can often be transformed into fibrous morphologies using fiber spinning techniques. Whether the fibrous morphology is of natural or artificial origin, the polysaccharide will often be present such that the fibers can be reduced to fibrillar and microfibrillar sub-morphologies through the application of energy.

Fibrillar and microfibrillar cellulose obtained in this manner have been considered for use in applications, including use as additives to aqueous-based systems in order to affect rheological properties, such as viscosity. The use level of these materials in aqueous systems is often on the order of about 2% by weight, below which these materials have a tendency to poorly occupy volume, and to exhibit gross inhomogeneities in distribution.

Microfibrillated cellulose and its manufacture are discussed in U.S. Pat. Nos. 4,500,546; 4,487,634; 4,483,743; 4,481,077; 4,481,076; 4,464,287; 4,452,722; 4,452,721; 4,378,381; 4,374,702; and 4,341,807, the disclosures of which are hereby incorporated by reference thereto. These documents, in part, purport to describe microfibrillated cellulose in stable, homogenous suspensions, characterized as useful in end use products including foods, cosmetics, pharmaceuticals, paints, and drilling muds.

Cellulose nanofibrils are characterized in WO 98/02486 (PCT/FR97/01290), WO 98/02487 (PCT/FR97/01291), and WO 98/02499 (PCT/FR97/01297), the disclosures of which are hereby incorporated by reference. Nanofibrils are characterized as having diameters in the range of about 2 to about 10 nanometers.

EP 845495 discusses cationic cellulose particulate which is characterized as insoluble, positively charged, and used in water treatment, specifically to treat water in a paper manufacturing plant. In paper making this cationic particulate is said to remove anionic trash from the water. The particles are obtained by milling, which is stated to reduce particle size uniformly such that particles are typically round as described by a length/diameter ratio of approximately 1. Particle size is stated to be 0.001 mm (i.e., 1 $\mu$m), and preferably 0.01 mm (10 $\mu$m)

EP 85901 1("EP '011") is directed to a process for obtaining cationic cellulose microfibrils or their soluble derivatives. The process is described as including making a cationic cellulose derivative and processing the derivative through a high pressure homogenizer to form transparent gels. The product can be dehydrated and rehydrated. Viscosity measurements are reported on the product at a concentration of 2% in water. EP '011 indicates that the degree of substitution ("DS") of the cellulose can range from 0.1 to 0.7, with a DS of between 0.2 and 0.7, 0.3 and 0.6, and 0.5 and 0.6 characterized as representing increasing orders of preference. The examples show cellulose with a DS ranging from a low of 0.24 up to 0.72. Gelling is reported to occur above a microfibril concentration of 10 g/L, or above 1%, in water. EP '011 defines gelling as occurring when G'>G", where G' is the dynamic storage modulus and G" is the dynamic loss modulus.

Microfibrillated chitosan is reported to form uniplanar, oriented sheets upon drying by H. Yokata, J. Polymer Sci., Part C: Polymer Letters, 24:423–425 (1986). This article mentions that at a level of 4% chitosan in water, a gel is formed having a viscosity of 26,600 cps (Brookfield, 20° C., rotor #7, 10 rpm). The microfibrillated chitosan is made by homogenization of commercial chitosan flakes in a Gaulin homogenizer. The commercial chitosan is deacetylated using sodium hydroxide.

JP 59 [1984]-84938 discusses a method for producing a chitosan suspension. Commercial chitosan separated and purified from crabs and lobsters is pulverized to pieces having maximum length of about 1–2 mm. The pieces are then suspended in water at up to 15% chitosan, and are run in multiple passes through a high pressure homogenizer at between 3,000 and 8,000 psi.

It would be desirable to obtain microfibrillar polysaccharides whose viscosity-affecting properties are achieved without the presence of cationic functionalities, at least in part because of the general lack of suitability of cationic materials for use in foods. It would also be desirable to obtain microfibrillar polysaccharides that are capable of forming a gel at concentrations of 1% or less, thereby providing economy and ease of formulation, while still providing necessary rheological behavior and homogeneity of distribution.

In addition, there is a continuing need in industry to improve the stability of commercial emulsions, such as paper sizing emulsions. At present, one method for stabilizing such emulsions is the addition of charged materials, such as cationic starches, which may be added in amounts equal to 10–20% by weight of the size component. Interaction with anionic components, such as sulfonates, can also improve stability. However, emulsion failure still takes place in such emulsions, either through density-driven separation, also referred to as creaming, or through gellation. It would accordingly be desirable to develop a material that could be added to emulsions to provide long-term stability.

SUMMARY OF THE INVENTION

The present intention is directed to derivatized microfibrillar polysaccharide, methods for its production, and applications for its use. The derivatized microfibrillar polysaccharides is derivatized to contain substituents that provide electrostatic and/or steric functionality; where electrostatic functionality is present, it includes, but is not necessarily limited to, the presence of anionic charge.

Polysaccharides suitable for use in the present invention include cellulose, hemicellulose, chitin, chitosan, guar gum, pectin, alginate, agar, xanthan, starch, amylose, amylopectin, alternan, gellan, mutan, dextran, pullulan, fructan, locust bean gum, carrageenan, glycogen, glycosaminoglycans, murein, bacterial capsular polysaccharides, and derivatives thereof. Mixtures of these may be employed. Preferred polysaccharides are cellulose, chitin, chitosan, pectin, agar, starch, carrageenan, and derivatives thereof, used singly or in combination, with cellulose being most preferred. The cellulose may be obtained from any available source, including, by way of example only, chemical pulps, mechanical pulps, thermal mechanical pulps, chemical-thermal mechanical pulps, recycled fibers, newsprint, cotton, soybean hulls, pea hulls, corn hulls, flax, hemp, jute, ramie, kenaf, manila hemp, sisal hemp, bagasse, corn, wheat, bamboo, velonia,,bacteria, algae, fungi, microcrystalline cellulose, vegetables, and fruits. Preferred sources of cellulose include purified, optionally bleached wood pulps produced from sulfite, kraft, or prehydrolyzed kraft pulping processes; purified cotton linters; fruits; and vegetables.

The derivatized microfibrillar polysaccharides that may be obtained using cellulose include, but are not limited to, hydroxyethyl cellulose, ethylhydroxyethyl cellulose, carboxymethylcellulose, carboxymethylhydroxyethyl cellulose, hydroxypropylhydroxyethyl cellulose, methyl cellulose, methylhydroxypropyl cellulose, methylhydroxyethyl cellulose, carboxymethylmethyl cellulose, hydrophobically modified carboxymethylcellulose, hydrophobically modified hydroxyethyl cellulose, hydrophobically modified hydroxypropyl cellulose, hydrophobically modified ethylhydroxyethyl cellulose, hydrophobically modified carboxymethylhydroxyethyl cellulose, hydrophobically modified hydroxypropylhydroxyethyl cellulose, hydrophobically modified methyl cellulose, hydrophobically modified methylhydroxypropyl cellulose, hydrophobically modified methylhydroxyethyl cellulose, hydrophobically modified carboxymethylmethyl cellulose, nitrocellulose, cellulose acetate, cellulose sulfate, cellulose vinyl sulfate, cellulose phosphate, and cellulose phosphonate.

The derivatized microfibrillar cellulose of the present invention may form a gel in water throughout the concentration range of between about 0.01% and about 100%, or throughout the concentration range of between about 0.01% and about 50% in water, or at least one point in the concentration range of from about 0.05% up to about 0.99% in water. In an alternative embodiment, the derivatized microfibrillar cellulose of the present invention forms a gel in water at a concentration of about 0.95%.

The derivatized microfibrillar polysaccharide may be used in the presence of a solvent, in which it is substantially insoluble. Examples of solvents include water, alcohol, and oil.

In the case of derivatization with groups that provide electrostatic functionality, the derivatized microfibrillar polysaccharides of the present invention may have a degree of substitution of less than about 0.5, less than about 0.35, less than about 0.2, less than about 0.18, or less than about 0.1. A preferred range for the degree of substitution is between about 0.02 and about 0.5, with a range of between about 0.05 and about 0.2 being more preferred. When the derivatized microfibrillar polysaccharide is derivatized to comprise substituents that provide electrostatic functionality in the form of anionic charge, the degree of substitution representing those substituents which provide electrostatic functionality in the form of anionic charge is preferably at least about 0.05. Anionic charge may be provided, for example, by carboxyl, sulfate, sulfonate, phosphonate, or phosphate groups, or combinations thereof. Where cationic charge is also present, both charges may be provided by the same groups or substituent (i.e., the substituent may be amphoteric or zwitterionic); or, the derivatized microfibrillar polysaccharide may be derivatized to contain both substituents that contain anionic charge and substituents that contain cationic charge. In addition, the derivatized microfibrillar polysaccharides of the present invention may be obtained by blending two or more separate derivatized microfibrillar polysaccharides, where at least one has been derivatized to provide anionic charge, and at least one other has been derivatized to provide anionic charge, cationic charge, or both.

When the derivatized microfibrillar polysaccharide of the present invention is derivatized to contain substituents that provide steric functionality, the derivatized microfibrillar polysaccharides may have a molar substitution of less than about 3.0, or of less than about 1.5, or of less than about 1.0, or of less than about 0.5. The range of molar substitution may be from about 0.5 to about 3.0. Steric functionality may be provided, by way of non-limiting example, by hydroxyethyl groups, hydroxypropyl groups, methyl groups, ethyl groups; straight- or branched-chain alkyl, alkenyl, or alkynyl groups having from about 4 to about 30 carbons; and/or aryl, arylalkyl, arylalkenyl, cyclic, and heterocyclic hydrocarbons having from about 4 to about 30 carbons.

In a preferred embodiment the derivatized microfibrillar polysaccharide contains carboxymethyl cellulose, and has a degree of substitution of less than about 2.0, preferably less than about 0.35. The range of degree of substitution may be from about 0.02 to about 0.2, with a range of from about 0.10 to about 0.2 being preferred.

The derivatized microfibrillar cellulose of the present invention may form a gel at a concentration of less than about 1% in water.

In a further embodiment, the present invention is directed to a comestible composition of matter containing the derivatized microfibrillar polysaccharide of the present invention. The comestible composition of matter may, by way of non-limiting example, be a low fat, reduced fat, or fat-free food spread, such as a mayonnaise, or a salad dressing. Alternatively, the comestible composition may contain a pharmaceutically active ingredient. The derivatized microfibrillar polysaccharide may be used to provide or improve a controlled, sustained, or delayed release of a component of the comestible composition, including in particular a pharmaceutically active ingredient.

In yet another embodiment, the derivatized microfibrillar polysaccharides of the present invention may be used in non-comestible, spreadable compositions of matter, such as skin care lotions or creams, or sunscreen lotions or creams.

The present invention is further directed to a paper composition containing the derivatized microfibrillar cellulose, and particularly, though not exclusively, microfibrillar carboxymethyl cellulose.

The derivatized microfibrillar polysaccharide may be produced by using a derivatizing step to treat a microfibrillar polysaccharide to obtain the derivatized microfibrillar polysaccharide. Alternatively, a derivatized polysaccharide may be microfibrillated to produce the derivatized microfibrillar polysaccharide. In another method, the steps of microfibrillation and derivatization may take place at substantially the same time. In a preferred embodiment, cellulose is first derivatized with monochloroacetic acid or a salt thereof under alkaline conditions to produce carboxymethylcellulose; the carboxymethylcellulose is suspended in water; and the resulting suspension is homogenized to produce microfibrillated carboxymethylcellulose.

The derivatizing step may include contacting a non-microfibrillar polysaccharide with a swelling agent, such as an anionic reagent, and may take place under alkaline conditions. These alkaline conditions may include contacting the cellulose with the anionic reagent in the presence of an alkaline reagent which is sodium hydroxide, an oxide or hydroxide of an alkali metal or alkaline earth metal, an alkali silicate, an alkali aluminate, an alkali carbonate, an amine, ammonium hydroxide, tetramethyl ammonium hydroxide, or combinations thereof. The derivatization may take place at high solids.

Microfibrillation may be accomplished by applying energy to a non-microfibrillar polysaccharide under conditions sufficient to produce microfibrillar polysaccharide. The non-microfibrillar may optionally be enzyme-treated before microfibrillizing. More specifically, microfibrillation may be accomplished using homogenization, pumping, mixing, heat, steam explosion, pressurization-depressurization cycle, impact, grinding, ultrasound, microwave explosion, milling, and combinations of these. In a preferred embodiment the non-microfibrillar polysaccharide is passed through a homogenizer under conditions sufficient to produce microfibrillar cellulose; those conditions may include a pressure differential of at least about 3,000 psi, and passing the non-microfibrillar polysaccharide through the homogenizer at least three times.

The method should be conducted to yield a derivatized microfibrillar polysaccharide that is substantially insoluble in the solvent of use. Water is a preferred solvent of use, but other solvents, including but not limited to alcohols and oils, are contemplated for various applications.

The present invention extends to derivatized microfibrillar polysaccharide produced by the above methods.

In an alternative embodiment the present invention is directed to a method of modifying the rheological properties of a liquid composition of matter by incorporating the derivatized microfibrillar polysaccharides of the present invention into the liquid composition of matter.

This may be accomplished by incorporating the derivatized microfibrillar polysaccharide into a water-containing system, where it may be used, for example, to provide scale control and/or corrosion control. The rheological properties which may be modified by the derivatized microfibrillar polysaccharide include viscosity, suspension stability, gel insensitivity to temperature, shear reversible gelation, yield stress, and liquid retention.

Liquid compositions which may be Theologically modified include, as non-limiting examples, foods, pharmaceuticals, neutraceuticals, personal care products, fibers, papers, paints, coatings, and construction compositions. These include oral care products; creams or lotions for epidermal application (such as moisturizing, night, anti-age, or sunscreen creams or lotions); food spreads, including reduced fat, low fat, or fat free food spreads (such as mayonnaises); and drilling fluids.

The present invention further extends to a method of improving the physical and/or mechanical properties of a coating composition by incorporating, into the coating composition, an effective amount of the derivatized microfibrillar polysaccharide. The physical and/or mechanical properties that may be improved in this manner include film forming, leveling, sag resistance, strength, durability, dispersion, flooding, floating, and spatter.

The present invention has particular utility in the field of paper manufacture and treatment. For example, derivatized microfibrillar cellulose may be used to improve one or more of sizing, strength, scale control, drainage, dewatering, retention, clarification, formation, adsorbency, film formation, membrane formation, and polyelectrolyte complexation during paper manufacture. As a particular example, the derivatized microfibrillar cellulose may be used as a drainage aid and/or as a sizing agent. A polyelectrolyte complex containing the derivatized microfibrillar polysaccharide is also within the scope of the present invention.

Microfibrillated carboxymethylcellulose is a particularly preferred embodiment for use in paper applications. During the process of paper manufacture, the derivatized microfibrillar cellulose may be used, by way of further example, in a papermaking machine to increase the rate of drainage and/or dewatering during paper manufacture; for retention of organic and/or inorganic dispersed particles in a sheet of paper during its manufacture; to improve the uniformity of formation of a sheet of paper during its manufacture; and to improve the strength of a sheet of paper. The derivatized microfibrillar cellulose may be used in combination with any of the additives and performance enhancers conventionally used in paper manufacture, including cationic polyacrylamides; polydiallyldimethylammonium chloride; cationic starch; derivatives of cellulose containing ammonium or mono-, di-, or trialkyl ammonium substituents; derivatives of guar gum containing ammonium or mono-, di-, or trialkyl ammonium substituents; resins formed by the reaction of amines and/or polyamines with epichlorohydrin; aluminum salts; hydrolyzed or partially hydrolyzed aluminum salts; complexes of hydrolyzed or partially hydrolyzed aluminum salts with organic or inorganic species; at least one polymer of ethylene oxide, ethyleneimine, allylamine, or vinylamine; and, at least one copolymer or terpolymer of ethylene oxide, ethyleneimine, allylamine, or vinylamine; and combinations thereof. In the context of retention of organic and/or inorganic dispersed particles, the particles so retained may include one or more of pulp fines, fillers, sizing agents, pigments, clays, detrimental organic particulate materials, and detrimental inorganic particulate materials.

In another embodiment, the stability of an emulsion, dispersion, or foam system may be improved by including, in the system, the derivatized microfibrillar polysaccharide of the present invention. The derivatized microfibrillar polysaccharide may be added to an existing system; added to a formulation which will be processed into such a system; or added during processing of such a formulation. Where addition takes place before completion of processing of a formulation into an emulsion, dispersion, or foam system, the processing conditions used to form the emulsion, dispersion, or foam may be used to produce the derivatized microfibrillar polysaccharide as well. Thus, a derivatized non-microfibrillated polysaccharide (where "non-microfibrillated" includes an incompletely microfibrillated polysaccharide) may be added to a formulation prior to completion of processing, and subsequent processing may then be conducted in a manner that will microfibrillate the polysaccharide. Alternatively, a microfibrillated polysaccharide may be added to the formulation, with subsequent processing conducted so as to derivatize the microfibrillated polysaccharide. In another variation, both derivatization and microfibrillation may take place during processing. Systems which may be treated in this manner include water-in-oil and oil-in-water emulsions.

The present invention also extends to emulsion, dispersion, and foam systems produced by the above methods; and, to emulsion, dispersion, or foam systems that contain the derivatized microfibrillar polysaccharide of the present invention.

DETAILED DESCRIPTION OF THE INVENTION

Figure 1:
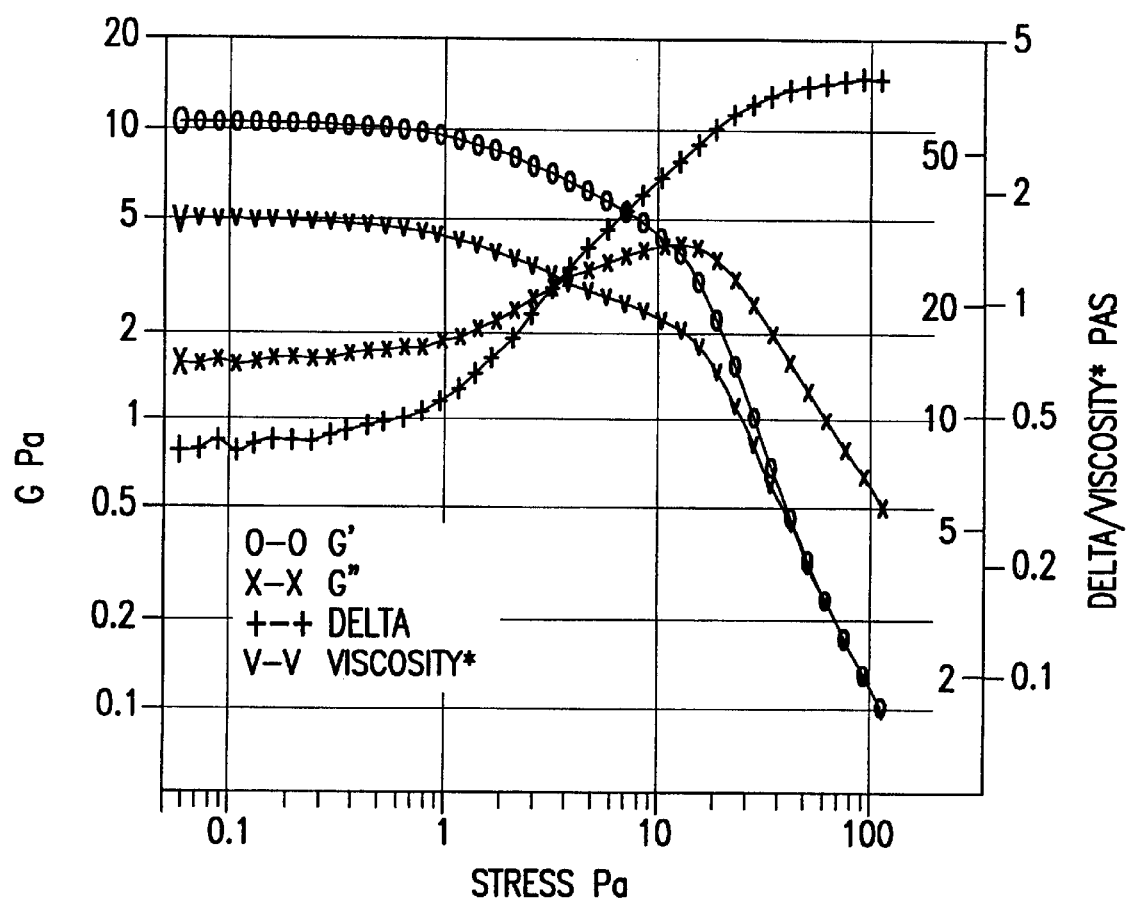
FIG. 1 shows the dynamic mechanical spectra of Example 7, Sample 1.

The present invention comprises derivatized microfibrillar polysaccharide. Suitable polysaccharides for use in the present invention include, without limitation, cellulose, hemicellulose, chitin, chitosan, guar gum, pectin, alginate, agar, xanthan, starch, amylose, amylopectin, alternan, gellan, mutan, dextran, pullulan, fructan, locust bean gum, carrageenan, glycogen, glycosaminoglycans, murein, bacterial capsular polysaccharides, and derivatives thereof, with cellulose being preferred. The polysaccharide may be used as is, or spinning may be used to generate or improve fibrous structure.

Cellulose is a preferred polysaccharide for use in the present invention. Sources of cellulose for use in this invention include the following: (a) wood fibers, such as from chemical pulps, mechanical pulps, thermal mechanical pulps, chemical-thermal mechanical pulps, recycled fibers, newsprint; (b) seed fibers, such as from cotton; (c) seed hull fiber, such as from soybean hulls, pea hulls, corn hulls; (d) bast fibers, such as from flax, hemp, jute, ramie, kenaf, (e) leaf fibers, such as from manila hemp, sisal hemp; (f) stalk or straw fibers, such as from bagasse, corn, wheat; (g) grass fibers, such as from bamboo; (h) cellulose fibers from algae, such as velonia; (i) bacteria or fungi; and () parenchymal cells, such as from vegetables and fruits, and in particular sugar beets, and citrus fruits such as lemons, limes, oranges, grapefruits. Microcrystalline forms of these cellulose materials may also be used. Preferred cellulose sources are (1) purified, optionally bleached, wood pulps produced from sulfite, kraft (sulfate), or prehydrolyzed kraft pulping processes, (2) purified cotton linters, and (3) fruits and vegetables, in particular sugar beets and citrus fruits. The source of the cellulose is not limiting, and any source may be used, including synthetic cellulose or cellulose analogs.

Cellulose is found in nature in several hierarchical levels of organization and orientation. Cellulose fibers comprise a layered secondary wall structure within which macrofibrils are arranged. Macrofibrils comprise multiple microfibrils which further comprise cellulose molecules arranged in crystalline and amorphous regions. Cellulose microfibrils range in diameter from about 5 to about 100 nanometers for different species of plant, and are most typically in the range of from about 25 to about 35 nanometers in diameter. The microfibrils are present in bundles which run in parallel within a matrix of amorphous hemicelluloses (specifically xyloglucans), pectinic polysaccharides, lignins, and hydroxyproline rich glycoproteins (includes extensin). Microfibrils are spaced approximately 3–4 nm apart with the space occupied by the matrix compounds listed above. The specific arrangement and location of the matrix materials and how they interact with the cellulose microfibrils is not yet fully known.

For purposes of the present invention polysaccharide microfibrils refer to small diameter, high length-to-diameter ratio substructures which are comparable in dimensions to those of cellulose microfibrils occurring in nature. By way of non-limiting example, polysaccharide microfibrils may have diameters in the range of about 20 to about 100 nanometers, combined with lengths providing high aspect ratios, such as in excess of 100, in excess of 500, or in excess of 1,000. While the present specification and claims refer to microfibrils and microfibrillation, the scope of the present invention also includes nanofibrils (cellulosic or otherwise), and the rheology modification, stabilization, and other properties that may be obtained with microfibrils by practicing the present invention may also be obtained using nanofibrils, either alone or in combination with microfibrils.

In nature many polysaccharides are not present in microfibril arrangements, however, by using fiber spinning techniques it is possible to manufacture fibers from these polysaccharides. In one embodiment of this invention it is contemplated that fibers spun from polysaccharides can be derivatized and microfibrillated into fibrous structures having dimensions on the order of those found naturally in cellulose. Further background on the structure, functions, and biogenesis of native cellulose may be found in Haigler, C.H., Cellular Chemistry and Its Applications, Nevell, pp. 30–83 (1985), the entirety of which is hereby incorporated by reference.

The derivatized microfibrillar polysaccharide of the present invention is characterized by being in microfibrillar form, and by the presence of substituents that provide steric and/or electrostatic functionality. The amount of substituent present may be quantified by the degree of substitution, or DS, in the case of some anionic and cationic substituents, and by the molar substitution, or MS, in the case of steric substituents. The degree of substitution, which will vary with the molecular weight of the polysaccharide, is the average number of substituted hydroxyl groups per anhydrosaccharide unit, while the molar substitution is the average number of substituent groups added per anhydrosaccharide unit. The DS and MS determine the solubility of the derivatized polysaccharide, and may be readily adjusted to obtain a derivatized polysaccharide that is substantially insoluble in the environment of use, whether aqueous or non-aqueous. While the environment of use will frequently be aqueous, the derivatized microfibrillar polysaccharides of the present invention have utility in applications having other solvents or liquid carriers, such as paints, coating, lacquers, oil-rich foods, inks (including but not limited to ink-jet inks), personal care products, cosmetics, and water-in-oil emulsions.

Any suitable method may be used to obtain the derivatized microfibrillar polysaccharide. In particular, the steps of microfibrillation and derivatization to impart steric and/or electrostatic functionality to the polysaccharide may be carried out separately or combined to arrive at the end result. Therefore, a non-microfibrillar polysaccharide starting material may either be derivatized with anionic groups, with both anionic and cationic groups, or with a blend or mixture of anionic groups and cationic groups, and then microfibrillated, or may first be microfibrillated and then derivatized. Alternatively, if the starting material is microfibrillar polysaccharide, only the derivatizing step would be necessary, whereas if the starting material is a polysaccharide that has already been properly derivatized with anionic or both anionic and cationic groups, only the microfibrillation step is required.

The degree of substitution (for electrostatic derivatization), and/or of molar substitution (for steric derivatization), of the polysaccharide should be sufficiently low so that the derivatized microfibrillar polysaccharide will be substantially insoluble in the solvent or carrier that is present in the intended environment of use. In many applications the solvent or carrier will be water, an such applications the degree of substitution and/or the molar substitution should be such that the derivatized microfibrillar polysaccharide is substantially insoluble in water. However, in other applications a polar solvent or carrier (such as an alcohol) may be used having different solubility characteristics, or a non-polar solvent or carrier (such as an oil) may be used, and in such cases the degree of substitution and/or the molar substitution should be adjusted to obtain a derivatized microfibrillar polysaccharide that is substantially insoluble in the solvent or carrier used in the application of interest, which, for purposes of convenience, will hereafter be referred to as the "solvent of use". Functionally, the derivatized microfibrillar polysaccharide should be sufficiently insoluble in the environment of use to provide the desired properties in the intended application.

Figure 9:
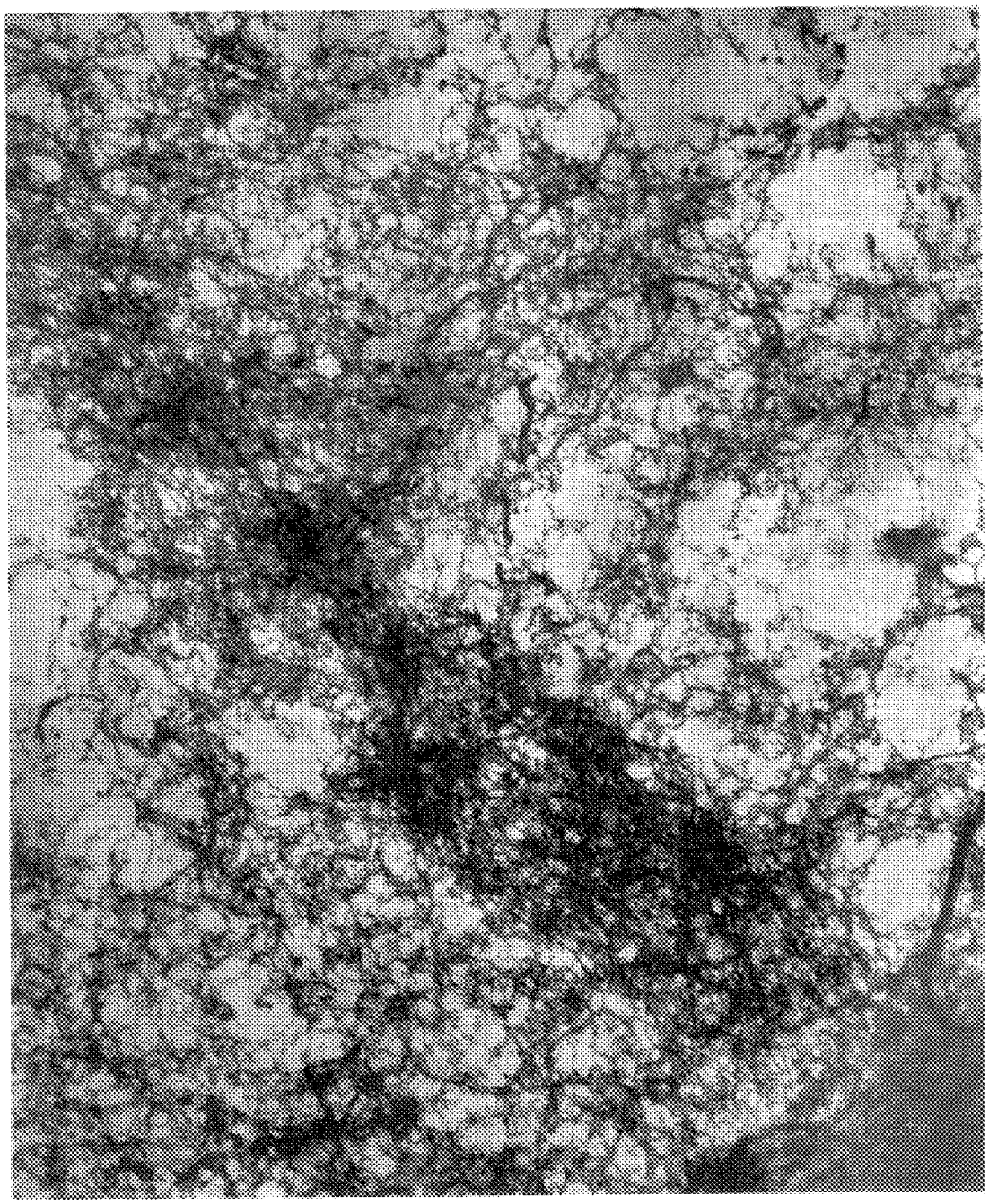
FIG. 9 is a transmission electron micrograph of a sample microfibrillar carboxymethylcellulose prepared as in example 3 below, with a degree of substitution of about 0.17, negative stained with urinal acetate, at a magnification of 10,000×.

The presence of substantially insoluble material may be confirmed by observation of a 1–5% suspension of the material in question in the solvent or carrier of use under a light microscope at sufficient magnification to see insoluble material. A size determination may be made by preparing a suspension of the material under consideration at approximately 0.1–0.01% in a liquid non-solvent which is effective in dispersing microfibrils. This suspension is then dried on a transmission electron microscope (TEM) grid, the sample is coated to protect it from electron beam damage, and examined at sufficient magnification and focus to observe structure in the 1–1000 nanometer range. If microfibrillar elements are present they can be detected under these conditions, and the combination of insolubility under the light microscope and microfibrillar structure under the TEM will indicate the presence of substantially insoluble microfibrillar material. See FIG. 9 for an example transmission electron micrograph of a microfibrillar carboxymethylcellulose prepared as in example 3 below, having a DS of about 0.17.

For purposes of simplicity, unless specifically indicated otherwise the term "substituents" shall be used herein to mean chemical species that provide steric stabilization to the polysaccharide; chemical species that provide electrostatic functionality to the polysaccharide through anionic charge; chemical species that provide electrostatic functionality to the polysaccharide through a combination of both anionic and cationic charge; and combinations of the foregoing. In addition, "electrostatic" means either anionic charge, or a combination of both anionic and cationic charge, whether as groups both present on a single substituent, or as groups provided separately on two or more substituents. "Derivatization" refers not only to chemical reactions resulting in covalent bonds, but to any process whereby the substituents become sufficiently associated with the polysaccharide to provide the rheological and other benefits of the present invention, and may include, for example, adsorption. Finally, references to the combination of both anionic and cationic charge on the polysaccharide include the use of substituents that contain both types of charge (i.e., amphoteric and/or zwitterionic substituents); the combined use of substituents which individually contain only anionic or only cationic charge, resulting in derivatized polysaccharide with a distribution of substituents that includes both anionic groups and cationic groups; and, blending of two or more derivatized polysaccharides where at least one derivatized polysaccharide includes at least anionic substituents and at least one other derivatized polysaccharide includes at least cationic substituents, resulting in a blend that contains both anionically derivatized polysaccharide and cationically derivatized polysaccharide. However, "derivatized" does not include the naturally-occurring, de minimis presence of groups that would only provide the steric and/or electrostatic functionality required by the present invention at concentrations higher than those found in nature. For example, naturally-occurring cellulose may contain very low levels of anionic charge, which may still be present after microfibrillation. However, such microfibrillated cellulose is not "derivatized" as that term is used in the present application, both because its degree of substitution has not been changed from its natural state, and because the amount of charge present in such microfibrillated cellulose would not provide the benefits of the present invention.

The sequence of steps used to arrive at the derivatized microfibrillar polysaccharide of the present invention is not critical. Therefore, the starting material used to make the derivatized microfibrillar polysaccharide may be in microfibrillar or non-microfibrillar form. Similarly, the starting material may already be derivatized with steric and/or electrostatic substituents, or not. If the starting material is non-microfibrillar polysaccharide, substituents may be placed on the polysaccharide followed by microfibrillation, or the microfibrillation may be carried out first, followed by the placement of the substituents onto the resulting microfibrils. It is also acceptable to process polysaccharide into fibrils, place the substituents on the fibrils, and then further process the fibrils into microfibrils. Similarly, any non-microfibrillar form of polysaccharide which already contains such substituents may be processed into microfibrillar form. Moreover, derivatization and microfibrillation may be carried out simultaneously.

It will be understood that most, if not all, polysaccharides will contain some quantity of both microfibrillar and non-microfibrillar structure both before and after processing, and that the ratio between the two structures may range from polysaccharide that is substantially completely microfibrillar, to polysaccharide that is substantially completely non-microfibrillar. As used herein, the terms "microfibrillar", "microfibrillated", and the like include polysaccharides that are substantially completely microfibrillated, and those which may be substantially microfibrillated while containing minor but significant amounts of non-microfibrillar structure, provided the polysaccharide is sufficiently microfibrillated to confer the benefits afforded by the present invention.

Processes which minimize the energy needed to produce microfibrils from non-microfibrillar starting material, and/or which reduce the amount of water extracted during the process or at its end, are preferred. In this regard, it should be noted that while the derivatized microfibrillar polysaccharide of the present invention can be made by derivatizing a microfibrillated polysaccharide, the microfibrillation process generally requires less energy, and/or is more efficient, if the polysaccharide has already been derivatized. Without being bound by theory, this may be because the presence of the steric and/or electrostatic functionalities on the polysaccharide 'loosens' the structure of fibril bundles.

The ability to use less energy not only offers cost savings, but results in less breakage of the polysaccharide microfibrils. Therefore, microfibrillating a polysaccharide that has already been derivatized may result in a derivatized microfibrillar polysaccharide with relatively longer microfibrils as compared to effecting derivatization after microfibrillation. This is particularly significant because the energy required for microfibrillation can be significantly reduced by amounts of derivatization which are below the level that would render the resulting derivatized microfibrillar polysaccharide freely soluble in water. For example, derivatization of cellulose resulting in a DS on the order of 0.1 or 0.2 will 'loosen' the fibril bundles in cellulose enough to permit microfibrillation using conventional shearing devices such as a homogenizer, impingement mixer, or ultrasonicator. These low DS cellulose microfibrils have diameters on the order of 50 nanometers combined with lengths of up to 500 microns, resulting in aspect ratios in excess of 1,000. While the low DS allows microfibrillation, it is too low to allow the resulting material to be fully soluble in the solvent or carrier of use at the concentrations of interest. Without being bound by theory, the presence of insoluble regions in the fibers may explain the data showing maximum gel formation at low DS's. These gels may be strengthened by weak association of the more hydrophobic unsubstituted regions.

The stabilization or derivatization is accomplished by the generation or placement of substituents onto the fibril and/or microfibril. It appears that the substituents become associated predominantly with the surface regions of the fibrils or microfibrils. Regardless of the precise mechanism, in functional terms microfibril-microfibril contact is inhibited by steric and/or electrostatic mechanisms or forces. The presence of the substituents also causes the microfibrils to occupy more volume than when they are not derivatized, possibly due to inhibition of contact along at least part of the length of the microfibrils. Rheological performance of the resulting derivatized microfibrillar polysaccharide is enhanced at low concentration since volume is better occupied and the materials are distributed more homogeneously.

With regard to use of steric force, steric functionality or stabilization is provided by the formation of a protective barrier or sheath around a particle (such as a cellulose fibril or microfibril) to prevent flocculation. For example, it may be achieved by a material, such as a polymer, being physically adsorbed on the surface of the particle, thereby preventing two particles from coming closer than a distance that is twice the sum of the radius of the particle and the thickness of the adsorbed layer. As two particles approach and the distance between them approaches the distance noted above, the adsorbed layers on two particles interact. This interaction, which as noted may be a polymer-polymer interaction, results in forces, such as osmotic and/or entropic forces, that repel the particles. This prevents flocculation of the two particles, providing stabilization. Because steric forces are generally provided by the size and/or configuration of the substituent, a substituent used to provide the polysaccharide with steric functionality or stabilization may be neutral, anionic, cationic, amphiphilic, amphoteric, and/or zwitterionic.

Without being bound by theory, the surfaces of the derivatized microfibrils appear to have some areas free of the substituents such that some limited interaction between microfibrils still takes place. Limited interaction may even be necessary to facilitate network formation, and may be a cause of the rheological attributes of interest such as yield stress, shear reversible gelation, and insensitivity of the modulus to temperature. It also appears that the length/diameter ratio, or aspect ratio, of the fibrils and microfibrils also contributes to the performance of the materials of the present invention.

Any suitable process may be used to generate or place the substituents on the polysaccharide. For convenience, the possible processes will generally be referred to collectively as "derivatization" herein; however, within the context of this invention, derivatization is used to mean any process which results in a polysaccharide (including fibrillar and microfibrillar polysaccharide) having the substituents sufficiently associated with the polysaccharide to provide the desired benefit(s), and includes not only chemical reactions resulting in covalent bonding, but also physical adsorption. In addition, the present application will refer both to "derivatization" and to "stabilization". Chemically, both terms refer to the same type of process, namely, the placement or generation of substituents on the cellulosic substrate. Functionally, "derivatization" is generally the broader term, as "stabilization" implies a functionality which is usually observed primarily or exclusively when the polysaccharide is in microfibrillar form.

Possible derivatization processes include any synthetic method(s) which may be used to associate the substituents with the polysaccharide. More generally, the stabilization or derivatization step may use any process or combination of processes which promote or cause the placement or generation of the substituents. For example, the conditions for treating non-microfibrillar polysaccharide should generally include both alkalinity and swelling of the polysaccharide, in order to make the surface of the fibrils more accessible to the placement or generation of the substituents. Alkalinity and swelling may be provided by separate agents, or the same agent may both provide alkalinity and cause swelling of the polysaccharide. In particular, alkaline agents often serve multiple purposes, in that they may catalyze the reaction between the polysaccharide and the substituent, optionally de-protonate the derivative, and swell open the polysaccharide structure to allow access of the reagents to carry out the derivatization.

Specific chemical methods which may be used to achieve the present invention include but are not limited to generation of anionic groups (such as carboxyl, sulfate, sulfonate, phosphonate, and/or phosphate); generation of both anionic and cationic groups (such as quaternary amine and/or amine); and generation of steric groups, on or near the surface of the particulate polysaccharide. Alkaline conditions are preferably obtained by using sodium hydroxide. Any material that functions as a solvent for the polysaccharide of choice may be used, and alternative alkaline agents include alkali metal or alkaline earth metal oxides or hydroxides; alkali silicates; alkali aluminates; alkali carbonates; amines, including aliphatic hydrocarbon amines, especially tertiary amines; ammonium hydroxide; tetramethyl ammonium hydroxide; lithium chloride; N-methyl morpholine N-oxide; and the like. In addition to catalytic amounts of alkaline agent, swelling agents may be added to increase access for derivatization. Interfibrillar and intercrystalline swelling agents are preferred, particularly swelling agents used at levels which give interfibrillar swelling, such as sodium hydroxide at an appropriately low concentration.

These derivatization reactions, if carried out on the original fibrous polysaccharide structure, may require specific conditions to maximize the efficiency of location of the derivatization onto the surface of the polysaccharide. For example, in the case of cellulose from wood pulp the concentration of the swelling agent used appears to have an effect on the performance of the final cellulose. In particular, in using sodium hydroxide it has been determined that the level of the sodium hydroxide can have a significant effect on the rheological performance.

It is preferred that derivatization of these fibrous polysaccharides be performed in a manner which limits the formation of microfibrils which are soluble in the intended end use composition, as these may not contribute significantly to the desired rheological performance. This typically limits the degree of derivatization which can be made where derivatization at higher levels would make the polysaccharide soluble in the end use composition. Specific limits may be readily determined based on the application in question, but as a matter of general guidance it is preferred that the degree of substitution (DS) be below about 0.5, or below about 0.35, or below about 0.2, or below about 0.18, or below about 0.1.

The derivatization may be carried out in any suitable manner, including but not limited to suspension in water; in organic solvent, either alone or in mixtures with water; in solution; and in high solids, either with water alone or with water and a minor amount of organic solvent. (For purposes of the present disclosure, "high solids" refers to a polysaccharide content of greater than about 25%.

Optional derivatizations or functionalities which may also be placed on the polysaccharide include but are not limited to short chain aliphatic and other hydrophobic-type substitutions; oligomeric and polymeric substitutions; uncharged substitutions, as for example short chain ethylene and propylene glycols; other associative-type functionality; surfactant-like functionality; methyl; ethyl; propyl; and combinations of these. These substitutions are optional in that they may not be intended for stabilization of the polysaccharide, and will instead provide additional functionality such as surface activity, emulsification power, adsorption characteristics, and the like.

The method for processing a non-microfibrillar form of polysaccharide into the microfibrillar form may be carried out either before or after the derivatization reaction. The preferred method involves the use of a homogenizer on a dilute suspension of the non-microfibrillar polysaccharide in an aqueous medium. The aqueous medium optionally may have additives such as swelling agents, in particular interfibrillar and/or intercrystalline swelling agents, for example sodium hydroxide, to aid in improving the ease of microfibril generation. A more preferred method of microfibrillation involves the use of mechanical energy on an aqueous suspension of derivatized polysaccharide which has not been dried. Other microfibrillation processes include, by way of non-limiting example, use of an impingement mixer; heat; steam explosion; pressurization-depressurization cycle; freeze-thaw cycle; impact; grinding (such as a disc grinder); pumping; mixing; ultrasound; microwave explosion; and milling. Combinations of these may also be used, such as milling followed by homogenization. Essentially any method of reducing particle size may be used, but methods for reducing particle size while preserving a high aspect ratio in the polysaccharide are preferred. As described previously, the degree of substitution of the polysaccharide also affects the ease of processing the polysaccharide to microfibrillar form.

The process to generate the particulate may either be run by the consumer in the final application such that the particulate is generated in situ, or be run as described above in aqueous media, the material dehydrated, and the resulting particulate dried. The dried particulate of this invention, hereafter referred to as the ready-to-gel or RTG form, can be rehydrated readily in polar solvents to obtain the desired theological attributes. Dehydration can be accomplished by displacing water with less polar solvents and drying, and can be accelerated by protonation or shielding of charged groups if they are present.

In terms of general properties, applications where the derivatized microfibrillar polysaccharide of the present invention have particular utility include those where the desired rheological attributes include at least one of yield stress, shear reversible gelation, and a modulus which is insensitive to temperature. The ability to provide the rheological attributes described herein also makes it possible to provide stabilization of mixtures of liquids and solids having different densities; gel-like properties, including mouth feel; pumpable gels; stabilization at elevated temperatures; and, control of hydration and diffusion.

In terms of more specific applications or fields of use, the utility of the present derivatized microfibrillar polysaccharides includes, without limitation, foods, personal care products, household products, pharmaceuticals, neutraceuticals, paper manufacture and treatment, coating compositions, water treatment, drilling fluids, agriculture, construction, and spill control and/or recovery.

In food applications, the derivatized microfibrillar polysaccharides of the present invention may be useful as rheology modifiers; as stabilizers, such as by inhibiting creaming or settling in suspensions; and as non-digestable dietary fiber. They may also be used to control ice crystal growth during, for example, ice cream manufacture and storage.

In personal care products, the derivatized microfibrillar polysaccharides may be used to stabilize emulsions, dispersions, suspensions, and foams, and may find use in creams, lotions, gels, and pastes, including those intended for epidermal application. Representative but not exhaustive examples include sunscreens; moisturizing or anti-aging creams and lotions; cleaning soaps or gels; antiperspirants and deodorants, including those in stick, pump spray, aerosol, and roll-on form; fragrance releasing gels; lipsticks, lip glosses, and liquid makeup products; oral care products, including toothpastes, tooth polishing and whitening agents, and denture care products such as cleaners and adhesives, and further including use in sorbitol, sorbitol-water mixtures, and glycerol-water mixtures; products where controlled, sustained, or delayed release of an ingredient would be desirable; wound care products, such as ointments (including anesthetic, antiseptic, and antibiotic ointments), dressings, and products such as ostomy rings where good liquid retention is desirable; and absorbent products, such as diapers. The present invention may have particular utility, not only in personal care products but in other applications, with products dispersed by a pumping action. The shear-reversible gelation exhibited by the derivatized microfibrillar polysaccharide is well suited for pump dispensing, and may be advantageously combined with its ability to stabilize emulsions, dispersions, and foams to improve the uniform delivery of product.

In the area of household products, the rheological properties of the present derivatized microfibrillar polysaccharides, and their ability to stabilize emulsions, dispersions, and foams, provide utility in areas such as detergents, shampoos, cleaners, and air fresheners. Specific examples include, without limitation, laundry products (including detergents, pre-spotting cleaners, and fabric treatment compositions, such as softeners); rug and upholstery shampoos; toilet bowl cleaners (particularly those dispensed in liquid or gel form); air fresheners; and general purpose cleaning agents, including liquids, gels, pastes, and foams used in cleaning and/or disinfecting household surfaces.

In pharmaceutical applications, the derivatized microfibrillar polysaccharides may have utility in controlled, sustained, or delayed release formulations; as disintegrants; as dietary fiber; in wound care, particularly in applications (such as ostomy rings) where liquid-holding ability is important; and as rheology modifiers.

In the area of paper manufacture and treatment, the derivatized microfibrillar polysaccharides of the present invention have utility in emulsion modification and/or stabilization; sizing; retention; clarification; absorbence; drainage; formation (such as by functioning as flocculation aids); deposit or scale control (by inhibiting the formation and/or growth of inorganic deposits); water treatment; dewatering; film and membrane formation; polyelectrolyte cross-linking; removal of detrimental organic and/or inorganic materials; in paper coatings; and in improving properties such as stiffness, wet strength, absorbancy, softness, toughness, tear resistance, and fold resistance.

In the context of paper manufacture, scale control refers to the prevention of calcium carbonate and calcium oxalate deposits forming during the pulping process. Scale control can be achieved by dispersion of salt crystals in the medium to prevent growth and deposition, inhibition of nucleation, or modification of the crystal growth mechanism to prevent the formation of crystal forms that will lead to deposits. The use of derivatized microfibrillar cellulose having micron and smaller particle size, stabilized with appropriate functional groups, would serve to control scale deposit because such microcarriers inhibit the crystal growth which leads to deposition. Moreover, cellulosic materials would be easier to recover from the pulping process due to their organic nature. Preferred functional groups would include phosphate/phosphonate groups, carboxylate groups, and sulfate/sulfonate groups. Alternative functional groups and appropriate use levels may be readily determined by those of ordinary skill in the art, based on the particular environment of use.

The derivatized microfibrillar cellulose may also be used in a papermaking machine to increase the rate of drainage and/or dewatering during paper manufacture; to retain organic and/or inorganic dispersed particles (such as pulp fines, fillers, sizing agents, pigments, and/or clays); to retain detrimental organic and inorganic particulate materials; to improve the uniformity of formation of a sheet of paper; and to improve the strength of a sheet of paper. With particular regard to drainage, drainage aids are additives that increase the rate at which water is removed from a paper slurry on a paper machine. These additives increase machine capacity, and hence profitability, by allowing faster sheet formation. Anionically charged microfibrillar cellulosic derivatives are capable of greatly increasing drainage, either alone or in combination with other charged polymers.

The derivatized microfibrillar cellulose of the present invention may also be used in coated papers, where cellulose derivatives may be used to control the rheology of the color coating and to provide water retention, thereby controlling the amount of liquid that permeates into the base sheet.

In coating compositions, such as paints and inks, the derivatized microfibrillar polysaccharides can provide rheology modification, improving properties such as spatter, leveling, sag resistance, flooding, and floating, and may have particular utility in gel paints. They may also improve pigment dispersion and/or stabilization, and function as charge control or flow control agents, including in inks, such as ink jet inks.

In the area of water treatment, the derivatized microfibrillar polysaccharides of the present invention can provide scale control, that is, inhibiting the formation and/or growth of inorganic deposits in aqueous systems; clarification; flocculation; sedimentation; coagulation; charge delivery; and softening.

In drilling fluids, the present derivatized microfibrillar polysaccharides can provide rheology modification, reduce or prevent fluid loss, and improve secondary oil recovery.

In agricultural applications, the derivatized microfibrillar polysaccharides of the present invention can be used in soil treatment, and may provide moisture retention, erosion resistance, frost resistance, and controlled, sustained, or delayed release of agricultural materials such as fertilizers, pesticides, fungicides, and herbicides. They may also be used for crop protection, such as to minimize or prevent frost damage.

In construction, the derivatized microfibrillar polysaccharides can be used in dry wall muds, caulks, water-soluble adhesives, and board manufacture.

In other areas, the derivatized microfibrillar polysaccharides can be used for control and cleanup of liquid spills, as absorbents for oil; in general, as stabilizers for emulsions, dispersions, and foams (including but not limited to oil-in-water and water-in-oil emulsions); and for emulsification. Stability of commercial emulsions, such as paper size emulsions, is a recurring issue in industry. Current commercial emulsions include those which generally consist of an oil, waxy, or rosin phase dispersed in water. These dispersions are generally stabilized by the addition of charged materials such as cationic starches, sodium lignin sulfonate, and aluminum sulfate. Such materials are generally added in amounts equal to about 10–20% by weight of the size component. The resulting dispersions are typically 0.2 to 2 micron particles, thought to be stabilized by charge repulsion, for example, with the positively charged starches on particle surfaces repelling each other.

One cause of emulsion failure is density-driven separation. This can be limited by increasing viscosity, or internal structure within the fluid. For example, an emulsion which maintains a viscosity of less than about 20 centipoise throughout a standard aging test might have its viscosity increased initially by as much as 100 centipoise through addition of a viscosifier to the formulation, and still be within acceptable commercial viscosity, provided that the viscosity did not then increase over time to exceed acceptable limits.

One method to accomplish this result would be to use a viscosifying agent that does not cause a substantial increase in viscosity when first added to an emulsion formulation, but which does provide an increase in viscosity during normal processing of the emulsion formulation to produce the emulsion. This can be accomplished by including, as an additive to the emulsion formulation, polysaccharide that has been derivatized as described herein but not yet microfibrillated. When the emulsion formulation is then subjected to energy, typically high shear, during the processing used to turn the emulsion formulation into an emulsion, the shear will also microfibrillize the derivatized polysaccharide, resulting in the derivatized microfibrillar polysaccharide of the present invention, which will be present as part of the emulsion. The gel produced by the derivatized microfibrillar polysaccharide will then thin under shear stress but re-form when shear stops. Moreover, the insolubility of such low DS/MS polysaccharide may cause it to concentrate at the oil/water interface of oil-andwater emulsions, rather than the aqueous bulk phase, which may be desirable.

Effectively the same result may be achieved by adding the derivatized microfibrillar polysaccharide of the present invention to an emulsion formulation, or to the final emulsion, or at any point during production of the emulsion. Further variations would include introducing derivatized polysaccharide that is only partially microfibrillated into the emulsion-making process at a point where subsequent processing would provide sufficient energy to complete the microfibrillation. It may also be possible to accomplish some or all of the derivatization as part of the emulsion production process; for example, the emulsion formulation may include a charged species that will adsorb onto the polysaccharide microfibrils, or such a species may be added during processing of the emulsion formulation, separately or in combination with the polysaccharide. Therefore, the derivatized microfibrillar polysaccharides of the present invention may serve as stabilizing additives to emulsions, with several process routes being available to accomplish this end result.

While the choice of method may cause some variation in the properties of the resulting emulsion, the basic benefit of improved emulsion stability should be achieved by any procedure which has, as its final result, the presence of the derivatized microfibrillar polysaccharide of the present invention in the final emulsion. Commercially, it may be desirable to supply customers with derivatized, non-microfibrillated polysaccharide as a powder which, when added to a formulation and subjected to high shear or other appropriate forms of energy, will microfibrillate and yield the derivatized microfibrillar polysaccharide of the present invention.

This improved emulsion stability may enable use of emulsion formulations which would not perform satisfactorily in the absence of the derivatized microfibrillar polysaccharide. Other benefits may include improved retention in paper, improved drainage of water from paper systems due to association of pulp and filler fines with the retained microfibrils, and resistance to emulsion breakage in the presence of high salt concentrations.

The subject electrostatically derivatized materials of this invention have also been discovered to provide rheology to aqueous systems over a wide pH range (namely from about 2.5 to 10 or higher) and ionic strength. This insensitivity to pH and ionic strength facilitates use in areas where low pH and high salt conditions exist, such as in personal care creams and lotions, food products, and the like.

In addition to the above, the derivatized microfibrillar polysaccharides of the present invention represent a vehicle for providing charge, whether anionic, cationic, or both, to a given environment. This may, as a representative example, have utility in water treatment, where charged particles are used to flocculate particulates and other contaminates.

The following examples indicate various possible methods for making and using the derivatized microfibrillar cellulose of present invention. These examples are merely illustrative, and are not to be construed as limiting the present invention to particular compounds, processes, conditions, or applications. Throughout this description, "gelling" is defined to occur when G'>G", where G' is the dynamic storage modulus and G" is the dynamic loss modulus. This is the functional definition used in EP '011; for general background, see Ferry, J. D., *Viscoelastic Properties of Polymers,* John E. Wiley & Sons, NY, 1980.

EXAMPLE 1

Comparative

Microfibrillated, Non-Derivatized Cellulose

The following three components were weighed into a one gallon jar at the following wt % levels:

|  | Weight | Weight % | Dry Wt. Basis |
|---|---|---|---|
| Bleached sulfate wood pulp (5.2% moisture) (Wayerhauser Company) | 74.82 g | 2.11 | 2.00 |
| Germaben ® II biocide (Sutton Laboratories, New Jersey) | 17.50 g | 0.49 | 0.49 |
| Deionized (DI) water | 3445.58 g | 97.39 | 97.50 |

The cellulose quickly settled to the bottom of the jar when there was no agitation of the slurry. The jar was shaken to disperse the solids. The slurry was then processed in a dual stage Gaulin Model 15MR homogenizer. The secondary stage was set at about 1000 psi and the primary stage was adjusted so that the total pressure was about 8000 psi. The slurry was processed for a total of 3.5 hours. The resulting slurry had a much thicker consistency and the cellulose remained suspended. When this suspension was diluted to 1.0% solids in DI water, the resulting suspension was a viscous slurry which did not exhibit gel properties. Over time the 1% suspension settled, leaving free water on the surface.

EXAMPLE 2

Preparation and Microfibrillation of Carboxymethylcellulose I (CMC I)

Isopropanol (IPA) and DI water were charged to a nitrogen sparged, jacketed resin kettle equipped with an air driven stirrer, stainless steel agitator, two pressure equalizing addition funnels, a reflux condenser, nitrogen inlet, vacuum line and thermocouple. Sulfate wood pulp (approximately 400 µm length) was added to the reactor and the mixture slurry was agitated for 10 minutes, after which the mixture was nitrogen sparged for 1 hour while cooling the slurry temperature to 15° C. The reactor was inerted. Aqueous 50% NaOH was slowly added to the reactor while maintaining the mixture slurry's temperature at about 15° C. The slurry was agitated for 1 hour after completion of caustic addition. Aqueous monochloroacetic acid (80% MCA) was slowly added to the reactor by funnel while maintaining reaction slurry temperature at about 15° C. After MCA addition, the reaction slurry was heated to 70° C. and held for 1.5 hours. The reaction slurry was cooled below 30° C. and glacial acetic acid was added to the reactor. The reaction mixture was then aspirator vacuum filtered with a sintered glass funnel and a rubber dam. The wetcake was slurried in 565 g of 80% methanol for 15 minutes using an air driven stirrer and a grounded stainless steel beaker and then aspirator vacuum filtered with a sintered glass funnel and a rubber dam. This was repeated two more times. The wetcake obtained from the previous three washes was slurried in 1000 g of pure methanol using an air driven stirrer and a grounded stainless steel beaker for 15 minutes to dehydrate and then aspirator vacuum filtered with a sintered glass funnel and rubber dam. The final wetcake was dried in a Lab-Line fluidized bed dryer (model number 23852) for 35 minutes (air-dry for 5 minutes, heat-dry at 50° C. for 10 minutes, and heat-dry at 70° C. for an additional 20 minutes) The carboxymethylcellulose (CMC) product was ground using a Retsch Grinding Mill (model 2M1) with a 1 mm screen. (Although the examples herein show washing of the product, the need for, or amount of, washing will depend on the intended application.)

TABLE 1

CMC I Recipes
(all weights in grams)

| Sample # | Cellulose Length | Wt. Cellulose (dry wt. Basis) | Wt. IPA | Wt. $H_2O$ | Wt. 50% NaOH (aq) | Wt. 80% MCA (aq) | Wt. Glacial Acetic Acid | DS |
|---|---|---|---|---|---|---|---|---|
| 1 | ~400 μm | 61.36 | 729 | 73.6 | 60 | 11.8 | 32.2 | 0.16 |
| 2 | ~400 μm | 61.36 | 729 | 73.6 | 60 | 11.8 | 32.2 | 0.18 |

Preparation of CMC slurry: An 800 g 1% CMC slurry was made from each Sample in Table 1 using the following materials:

| | Weight | Weight % |
|---|---|---|
| CMC | 8.00 grams | 1.0 ± 0.06% |
| Germaben ® II biocide | 4.00 grams | 0.5% |
| Deionized water | 788.00 grams | 98.5 ± 0.06% |
| Total | 800.00 grams | |

The container was closed and shaken to wet and disperse the CMC solids. The solids will settle if left standing, so the container was shaken just prior to pouring the slurry into the homogenizer.

Homogenization of CMC slurries: The suspension was processed in the homogenizer equipped with an agitated feed pot as follows: the homogenizer was turned on before the slurry was loaded. An 800 gram slurry was processed for about 20 minutes at about 3000 psi by recycling the discharged stream from the homogenizer to the feed pot. Pressure was monitored and appropriate adjustments made to the primary stage handwheel to keep the total pressure at about 3000 psi. After the processing was completed, the discharge tube was redirected so that the sample was collected and stored in a capped jar.

Rheological testing of microfibrillated CMC I: Each microfibrillated CMC sample prepared in Example 2 was then tested for rheological properties. Data was collected on a Bohlin CS Rheometer (Bohlin Instruments, Cranbury, N.J.). Dynamic mechanical properties were measured including the dynamic storage modulus, the dynamic loss modulus, complex viscosity, and yield stress.

Rheometer Test Conditions

Temperature Sweep: Measuring System: PP 40; 25° C.–65° C.; Shear Stress: automatic; Frequency: 1 Hz; Temperature Ramp Rate: 5° C./60 seconds; Measurement Interval: 20 seconds; Gap: 1 mm.

Yield Stress Test: Measuring System: CP 4/40; Stress: 6.0E-02–1.0E+02; Sweep Time: 60.0 seconds; Number of Steps: 30; Temperature: Manual (25° C.); No of measurements: 1; Measurement Interval: 5 seconds.

Stress Sweep Test: Measuring System: PP 40; Temperature: Manual (25° C.); Number of Measurements: 1; Gap: 1 mm; Measurement Interval: 5 seconds; Frequency: 1 Hz.

TABLE 2

Rheology of Microfibrillated CMC I

| Sample # | Cellulose Length | DS of CMC I | Yield Stress (Pa) | G' @ 5.75 Pa (Pa) |
|---|---|---|---|---|
| 1 | ~400 μm | 0.16 | 8.08 | 256 |
| 2 | ~400 μm | 0.18 | Not Tested | 192 |

A copy of the dynamic mechanical spectra (obtained by the stress sweep test) of Sample 1 is given in FIG. 1.

EXAMPLE 3

Preparation and Microfibrillation of Carboxymethylcellulose II (CMC II)

Isopropanol (IPA) and DI water were charged to a nitrogen sparged, jacketed resin kettle equipped with an air driven stirrer, stainless steel agitator, two pressure equalizing addition funnels, a reflux condenser, nitrogen inlet, vacuum line and thermocouple. Sulfate wood pulp (approximately 400 μm length) was added to the reactor, the mixture slurry was agitated for 10 minutes, after which the mixture was nitrogen sparged for 1 hour while cooling the slurry temperature to 15° C. The reactor was inerted. Aqueous 50% NaOH was slowly added to the reactor maintaining the mixture slurry's temperature at about 15° C. The slurry was agitated for 1 hour after completion of caustic addition. Aqueous monochloroacetic acid (80% MCA) was slowly added to the reactor by funnel while maintaining reaction slurry temperature at about 15° C. After MCA addition, the reaction slurry was heated to about 70° C. and held for 1.5 hours. The reaction slurry was cooled down to below 30° C. and then aspirator vacuum filtered with a sintered glass funnel and a rubber dam. The wetcake was slurried in 565 g of 80% methanol for 15 minutes using an air driven stirrer and a grounded stainless steel beaker and then aspirator vacuum filtered with a sintered glass funnel and a rubber dam. This was repeated two more times. The wetcake obtained from the previous three washes was slurried in 1000 g of pure methanol using an air driven stirrer and a grounded stainless steel beaker for 15 minutes to dehydrate and then aspirator vacuum filtered with a sintered glass funnel and rubber dam. The final wetcake was dried in a Lab-Line fluidized bed dryer (model number 23852) for 35 minutes (air-dry for 5 minutes, heat-dry at 50° C. for 10 minutes, and heat-dry at 70° C. for an additional 20 minutes). The carboxymethylcellulose (CMC) product was ground using a Retsch Grinding Mill (model 2M 1) with a 1 mm screen.

TABLE 3

CMC II Recipes
(all weights in grams)

| Sample # | Cellulose Length | Wt Cellulose (dry wt. Basis) | Wt. IPA | Wt. H₂O | Wt. 50% NaOH (aq) | Wt. 80% MCA (aq) | DS |
|---|---|---|---|---|---|---|---|
| 1 | ~400 μm | 77.11 | 937.5 | 141.64 | 12.50 | 8.63 | 0.04 |
| 2 | ~400 μm | 61.69 | 750 | 113.32 | 10.00 | 6.90 | 0.06 |
| 3 | ~400 μm | 77.11 | 937.5 | 141.64 | 25.00 | 17.25 | 0.13 |
| 4 | ~400 μm | 61.91 | 750 | 113.09 | 20.00 | 13.95 | 0.15 |
| 5 | ~400 μm | 61.30 | 750 | 113.71 | 20.00 | 13.86 | 0.16 |
| 6 | ~400 μm | 61.91 | 750 | 113.09 | 20.00 | 13.79 | 0.17 |
| 7 | ~400 μm | 61.43 | 750 | 113.58 | 23.60 | 16.27 | 0.19 |
| 8 | ~400 μm | 61.62 | 750 | 109.38 | 28.00 | 19.32 | 0.23 |
| 9 | ~400 μm | 61.88 | 750 | 108.12 | 30.00 | 20.70 | 0.28 |
| 10 | ~400 μm | 61.43 | 750 | 106.08 | 35.00 | 24.15 | 0.31 |
| 11 | ~400 μm | 61.43 | 750 | 108.58 | 30.00 | 20.70 | 0.34 |
| 12 | ~200 μm | 62.60 | 750 | 116.41 | 12.00 | 8.28 | 0.10 |
| 13 | ~200 μm | 62.60 | 750 | 112.91 | 19.00 | 13.11 | 0.17 |

Slurry preparation and homogenizer processing were performed as in example 2. Rheological testing was performed as described in example 2.

TABLE 4

Rheology of Microfibrillated CMC II

| Sample # | Cellulose Length | DS of CMC I | Yield Stress (Pa) | G' @ 5.75 Pa (Pa) | G' @ 25° C./50° C. (Pa) |
|---|---|---|---|---|---|
| 1 | ~400 μm | 0.04 | Not Tested | 125 | 145/168 |
| 2 | ~400 μm | 0.06 | Not Tested | 139 | 161/160 |
| 3 | ~400 μm | 0.13 | 18.0 | 467 | 508/493 |
| 4 | ~400 μm | 0.15 | Not Tested | 467 | 441/429 |
| 5 | ~400 μm | 0.16 | 18.1 | 474 | 436/450 |
| 6 | ~400 μm | 0.17 | 34.7 | 436 | 452/462 |
| 7 | ~400 μm | 0.19 | 28.1 | 306 | 331/352 |
| 8 | ~400 μm | 0.23 | 21.4 | 148 | 137/145 |
| 9 | ~400 μm | 0.28 | 18.0 | 114 | Not Tested |
| 10 | ~400 μm | 0.31 | 14.7 | 12.9 | 12.3/12.6 |
| 11 | ~400 μm | 0.34 | 11.4 | 19 | 23.4/24.9 |
| 12 | ~200 μm | 0.10 | 8.08 | 339 | Not Tested |
| 13 | ~200 μm | 0.17 | 16.1 | 354 | Not Tested |

Figure 2:
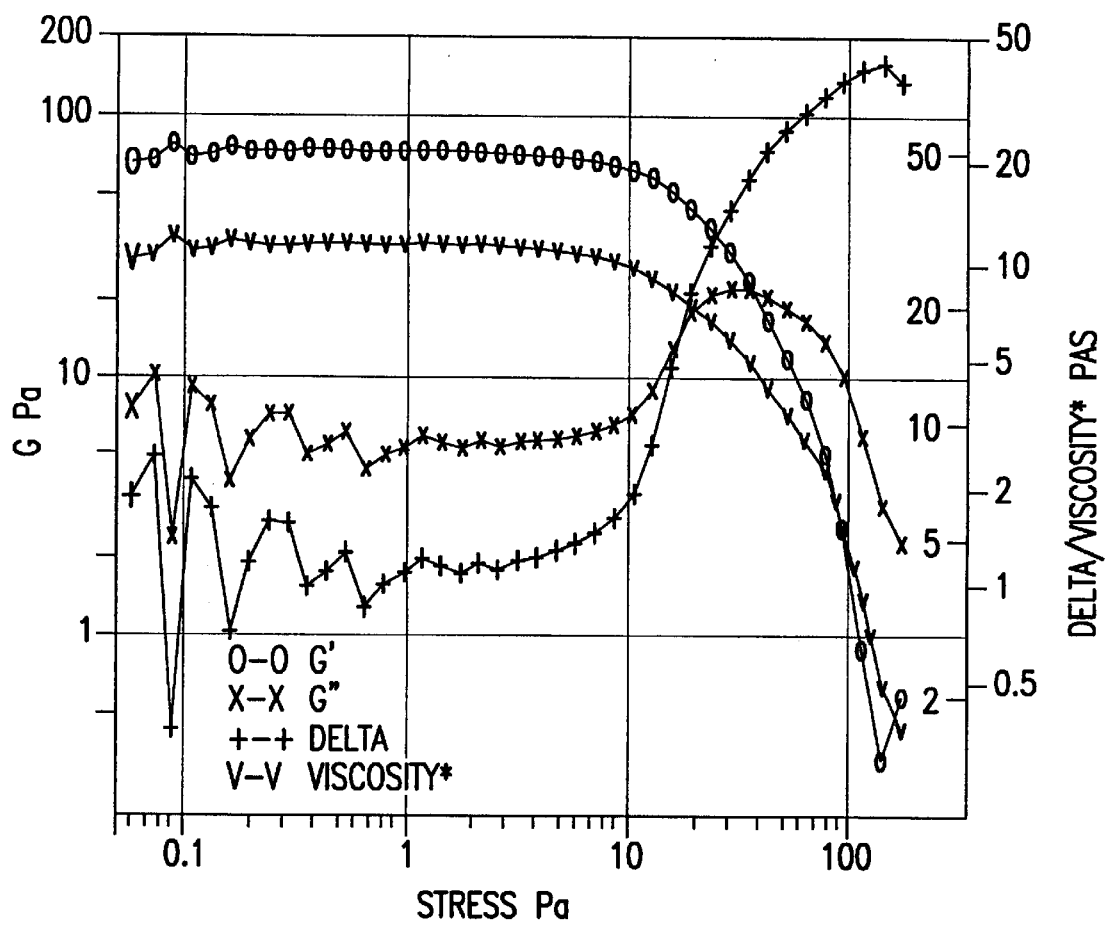
FIG. 2 shows the dynamic mechanical spectra of Example 7, Sample 2.

A copy of the dynamic mechanical spectra (obtained by the stress sweep test) of Sample 3 is given in FIG. 2.

EXAMPLE 4

Preparation and Microfibrillation of Carboxymethylcellulose III (CMC III).

Isopropanol and DI water were charged to a nitrogen sparged, jacketed resin kettle equipped with an air driven stirrer, stainless steel agitator, two pressure equalizing addition funnels, a reflux condenser, nitrogen inlet, vacuum line and thermocouple. Sulfate wood pulp (approximately 400 μm length) was added to the reactor, the mixture slurry was agitated for minutes, after which the mixture was nitrogen sparged for 1 hour while cooling the slurry temperature to about 15° C. The reactor was inerted. Aqueous NaOH (50% NaOH) was slowly added to the reactor maintaining the mixture slurry's temperature at about 15° C. The slurry was agitated for 1 hour after completion of caustic addition. Aqueous sodium monochloroacetate was prepared by mixing 80% MCA, 50% aqueous NaOH and DI water. This solution was slowly added to the reactor by addition funnel while maintaining reaction slurry temperature at about 15° C. After MCA addition, the reaction slurry was heated to about 70° C. and held for 1.5 hours. The reaction slurry was cooled down to below 30° C. and then aspirator vacuum filtered with a sintered glass funnel and a rubber dam. The wetcake was slurried in 565 g of 80% methanol for 15 minutes using an air driven stirrer and a grounded stainless steel beaker and then aspirator vacuum filtered with a sintered glass funnel and a rubber dam. This was repeated two more times. The wetcake obtained from the previous three washes was slurried in 1000 g of pure methanol using an air driven stirrer and a grounded stainless steel beaker for 15 minutes to dehydrate and then aspirator vacuum filtered with a sintered glass funnel and rubber dam. The final wetcake was broken into small particles using a rubber spatula and then dried in the fluidized bed dryer for 35 minutes. (Air-dry for 5 minutes, heat-dry at 50° C. for 10 minutes and heat-dry at 70° C. for an additional 20 minutes) The product was ground using the Retsch mill with a 1 mm screen.

TABLE 5

CMC III Recipes
(all weights in grams)

| Sample # | Cellulose Length | Wt Cellulose (dry wt. basis) | Wt. IPA | Wt. H₂O | Wt. 50% NaOH (aq) | NaMCA Solution 80% MCA | NaMCA Solution 50% NaOH | NaMCA Solution H₂O | DS |
|---|---|---|---|---|---|---|---|---|---|
| 1 | ~400 μm | 61.88 | 750 | 117.12 | 6.39 | 8.28 | 5.61 | 3.0 | 0.06 |
| 2 | ~400 μm | 61.88 | 750 | 114.32 | 9.38 | 12.14 | 8.22 | 5.0 | 0.12 |
| 3 | ~400 μm | 61.62 | 750 | 113.38 | 12.58 | 16.27 | 11.02 | 10.0 | 0.16 |
| 4 | ~400 μm | 61.62 | 750 | 108.38 | 15.98 | 20.70 | 14.02 | 10.0 | 0.24 |
| 5 | ~400 μm | 61.62 | 750 | 105.88 | 18.64 | 24.15 | 16.36 | 10.0 | 0.29 |
| 6 | ~400 μm | 61.88 | 750 | 102.47 | 21.31 | 27.60 | 18.69 | 10.0 | 0.31 |
| 7 | ~200 μm | 62.60 | 750 | 116.41 | 6.39 | 8.28 | 5.61 | 10.0 | 0.08 |
| 8 | ~200 μm | 62.60 | 750 | 112.91 | 10.12 | 13.11 | 8.88 | 10.0 | 0.16 |
| 9 | ~200 μm | 62.60 | 750 | 110.61 | 12.57 | 16.28 | 11.03 | 10.0 | 0.21 |
| 10 | ~200 μm | 62.60 | 750 | 117.12 | 15.67 | 20.30 | 13.75 | 10.0 | 0.26 |

Slurry preparation and homogenizer processing were performed as in example 2 except for Sample #7, which was processed for 30 minutes. Rheological testing was performed as described in example 2.

TABLE 6

Rheology of Microfibrillated CMC III

| Sample # | Cellulose Length | DS of CMC III | Yield Stress (Pa) | G' @ 5.75 Pa (Pa) | G' @ 25° C./50° C. (Pa) |
|---|---|---|---|---|---|
| 1 | ~400 μm | 0.06 | 14.7 | 281 | 316/310 |
| 2 | ~400 μm | 0.12 | 51.4 | 568 | 520/586 |
| 3 | ~400 μm | 0.16 | 28.1 | 564 | 607/649 |
| 4 | ~400 μm | 0.24 | 18.1 | 457 | 414/474 |
| 5 | ~400 μm | 0.29 | 21.4 | 298 | 292/303 |
| 6 | ~400 μm | 0.31 | 44.7 | 288 | Not Tested |
| 7 | ~200 μm | 0.08 | 4.70 | 238 | Not Tested |

TABLE 6-continued

Rheology of Microfibrillated CMC III

| Sample # | Cellulose Length | DS of CMC III | Yield Stress (Pa) | G' @ 5.75 Pa (Pa) | G' @ 25° C./50° C. (Pa) |
|---|---|---|---|---|---|
| 8 | ~200 μm | 0.16 | 29.5 | 483 | Not Tested |
| 9 | ~200 μm | 0.21 | 18.1 | 339 | Not Tested |
| 10 | ~200 μm | 0.26 | 21.4 | 288 | Not Tested |

[1] 30 minute homogenizer processing time.

Figure 3:
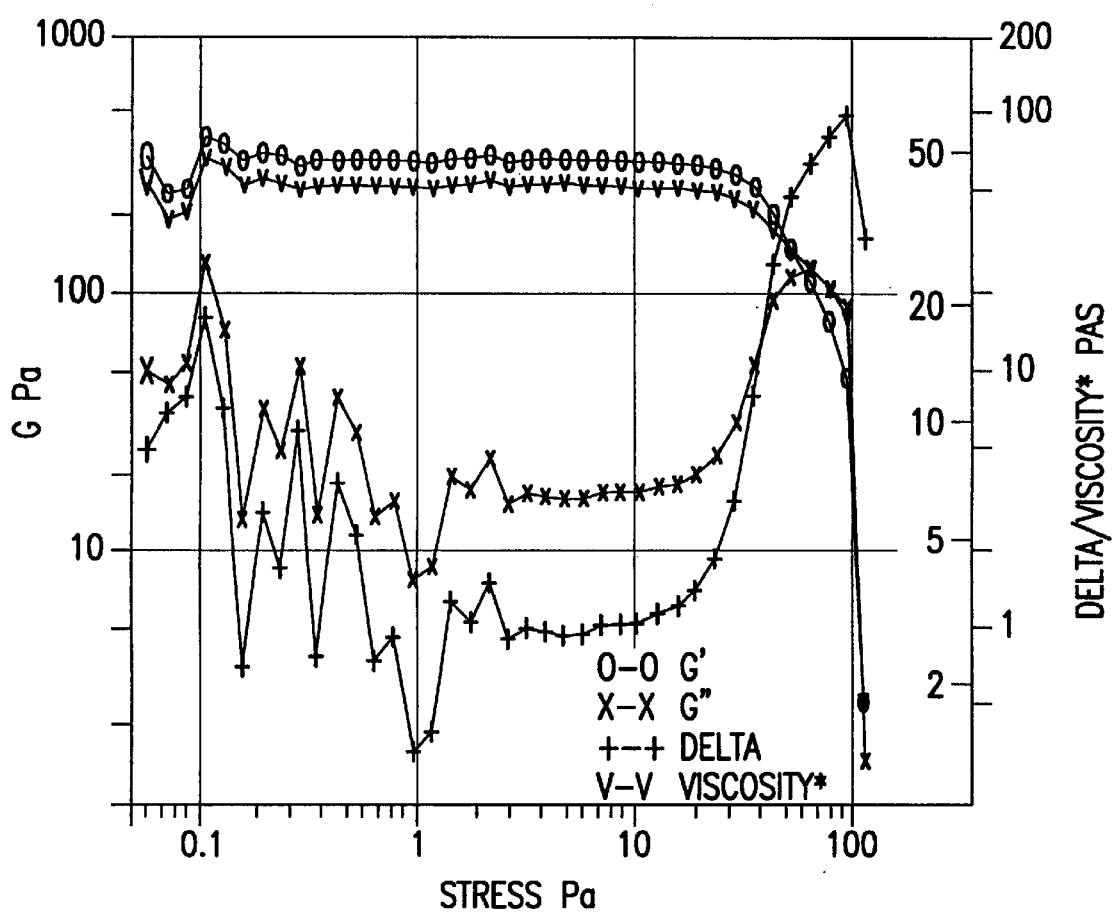
FIG. 3 shows the dynamic mechanical spectra of Example 7, Sample 3.

A copy of the dynamic mechanical spectra (obtained by the stress sweep test) of Sample 3 is given in FIG. 3.

EXAMPLE 5

CMC Preparation with Water Washing of Wetcake

Isopropanol and DI water were charged to a nitrogen sparged, jacketed resin kettle equipped with an air driven stirrer, stainless steel agitator, two pressure equalizing addition funnels, a reflux condenser, nitrogen inlet, vacuum line and thermocouple. Sulfate wood pulp (approximately 400 μm length) was added to the reactor, the mixture slurry was agitated for 10 minutes, after which the mixture was nitrogen sparged for 1 hour while cooling the slurry temperature to 15° C. The reactor was inerted. Aqueous NaOH (50% NaOH) was slowly added to the reactor maintaining the mixture slurry's temperature at about 15° C. The slurry was agitated for 1 hour after completion of caustic addition. Aqueous sodium monochloroacetate was prepared by mixing 80% MCA, 50% aqueous NaOH and DI water. This solution was slowly added to the reactor by addition funnel while maintaining reaction slurry temperature at about 15° C. After MCA addition, the reaction slurry was heated to about 70° C. and held for 1.5 hours. The reaction slurry was cooled down to below 30° C. and then aspirator vacuum filtered with a sintered glass funnel and a rubber dam. The wetcake was slurried in 650 g of DI water for 15 minutes using an air driven stirrer and a grounded stainless steel beaker and then aspirator vacuum filtered with a sintered glass funnel and a rubber dam. This was repeated one additional time. The wetcake obtained from the previous two washes was slurried in 1000 g DI water using an air driven stirrer and a grounded stainless steel beaker for 15 minutes and then aspirator vacuum filtered with a sintered glass funnel and rubber dam. The final wetcake was dried in the fluidized bed dryer for 35 minutes (air-dry for 5 minutes, heat-dry at 50° C. for 10 minutes and heat-dry at 70° C. for an additional 20 minutes). The product was ground using the Retsch mill with a 1 mm screen.

TABLE 7

Water Washed CMC Recipes (all weights in grams)

| Sample # | Wt Cellulose (dry wt. Basis) | Wt. IPA | Wt. H$_2$O | Wt. 50% NaOH (aq) | 80% MCA | NaMCA Solution 50% NaOH | H$_2$O | DS |
|---|---|---|---|---|---|---|---|---|
| 1 | 61.88 | 750 | 110.5 | 10.12 | 13.11 | 8.88 | 10.0 | 0.10 |
| 2 | 60.06 | 750 | 110.5 | 10.12 | 13.11 | 8.88 | 10.0 | 0.13 |

Slurry preparation, homogenizer processing, and rheological testing were performed as described in example 2.

TABLE 8

Rheology of Water Washed CMC Samples

| Sample | DS of CMC | Yield Stress (Pa) | G' @ 5.75 Pa (Pa) |
|---|---|---|---|
| 1 | 0.10 | 37.4 | 724 |
| 2 | 0.13 | 34.7 | 855 |

Figure 4:
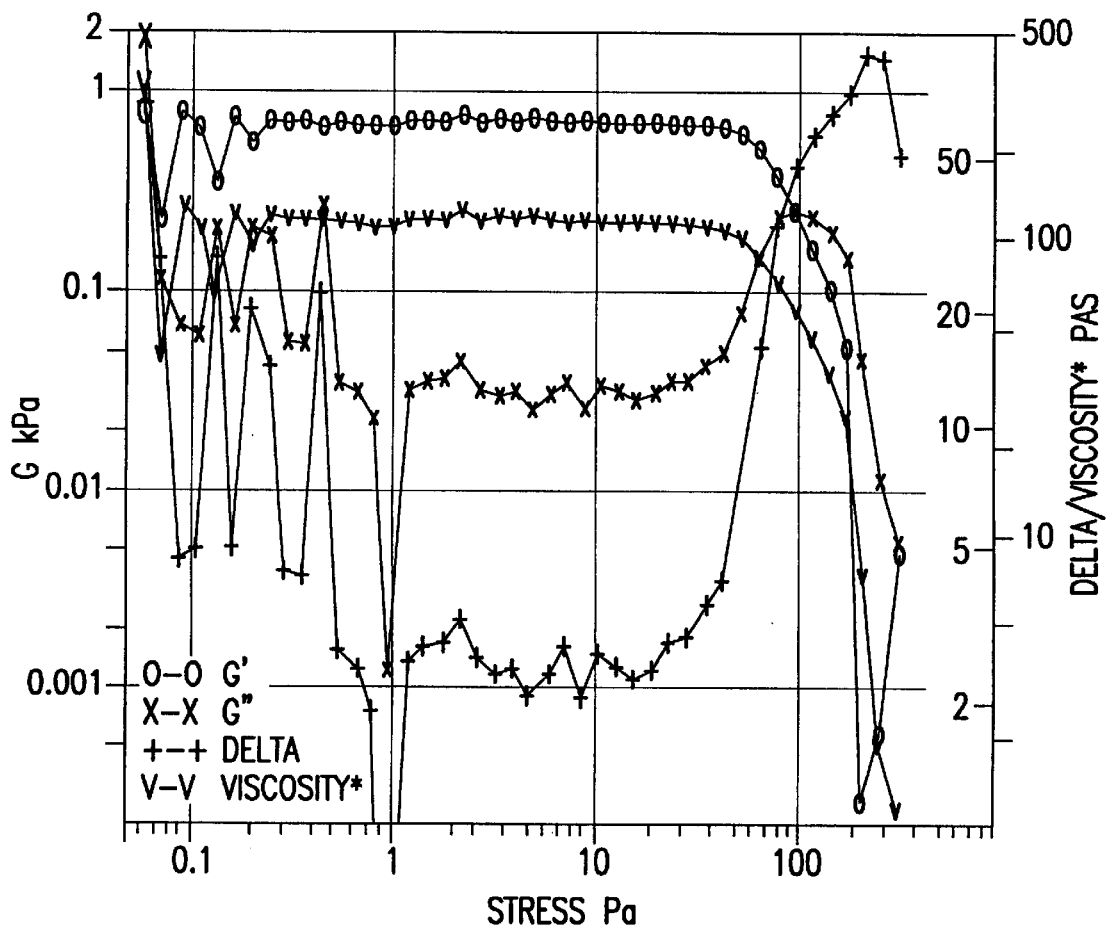
FIG. 4 shows the dynamic mechanical spectra of Example 7, Sample 4.

A copy of the dynamic mechanical spectra (obtained by the stress sweep test) of Sample 2 is given in FIG. 4.

EXAMPLE 6

High Solids Reactions

Sulfate wood pulp (about 200 μm length) was charged to an Abbey Ribbon Blender (model 0 RM, Paul O. Abbe, Inc., Little Falls, N.J.) equipped with a spray nozzle. The reactor was sealed and the system was inerted with nitrogen under slow agitation. Agitation was increased to approximately 125 rpm and a solution of 50% aqueous NaOH and DI water was sprayed into the reactor. The mixture was mixed for one hour at ambient temperature. An aqueous solution of sodium monochloroacetate (NaMCA) was sprayed into the reactor and the reactor temperature was increased to 75° C. and held for 2 hours. Glacial acetic acid was sprayed into the reactor and the reactor was cooled to approximately 30° C. The product was slurried in 3 liters of water for 15 minutes and filtered using a rubber dam. This slurry/filtration process was repeated three additional times. The final filter cake was dried in the fluidized bed dryer and ground in the Retsch mill using a 1 mm screen.

TABLE 9

High Solids Recipes
(all weights in grams)

| Sample | Wt. Cellulose (dry wt. Basis) | Wt. $H_2O$ | Wt. 50% NaOH (aq) | Wt. NaMCA (NaMCA/$H_2O$) | Acetic Acid | DS |
|---|---|---|---|---|---|---|
| 1 | 500 | 93 | 62.8 | 105/128.3 | 0 | 0.10 |
| 2 | 180 | 64.8 | 43.2 | 45.3/55.4 | 8.6 | 0.17 |

Slurry preparation: As in Example 2, except that Sample #2 (DS=0.17) was worked up as a 10% solids slurry in water. This slurry was then mixed with more water and Germaben® II to make the new slurry which was processed in the homogenizer.

|  | Weight | Weight % |
|---|---|---|
| 10% CMC slurry | 80.07 grams | 10 00% |
| Germaben ® II biocide | 4.01 grams | 0.50% |
| Deionized water | 716.88 grams | 89.50% |
| Total | 800.96 grams | |

Since the final slurry is 10% by weight of a 10% CMC slurry, the actual CMC level is the normal 1% by weight. Homogenization was performed as in Example 2 except that Sample #1 was processed for 25 minutes, and Theological testing was performed as in example 2.

TABLE 10

Rheology of High Solids Samples

| Sample | DS of CMC | Yield Stress (Pa) | G' @ 5.75 Pa (Pa) |
|---|---|---|---|
| 1 | 0.10 | 18.1 | 248 |
| 2 | 0.17 | 31.4 | 427 |

Figure 5:
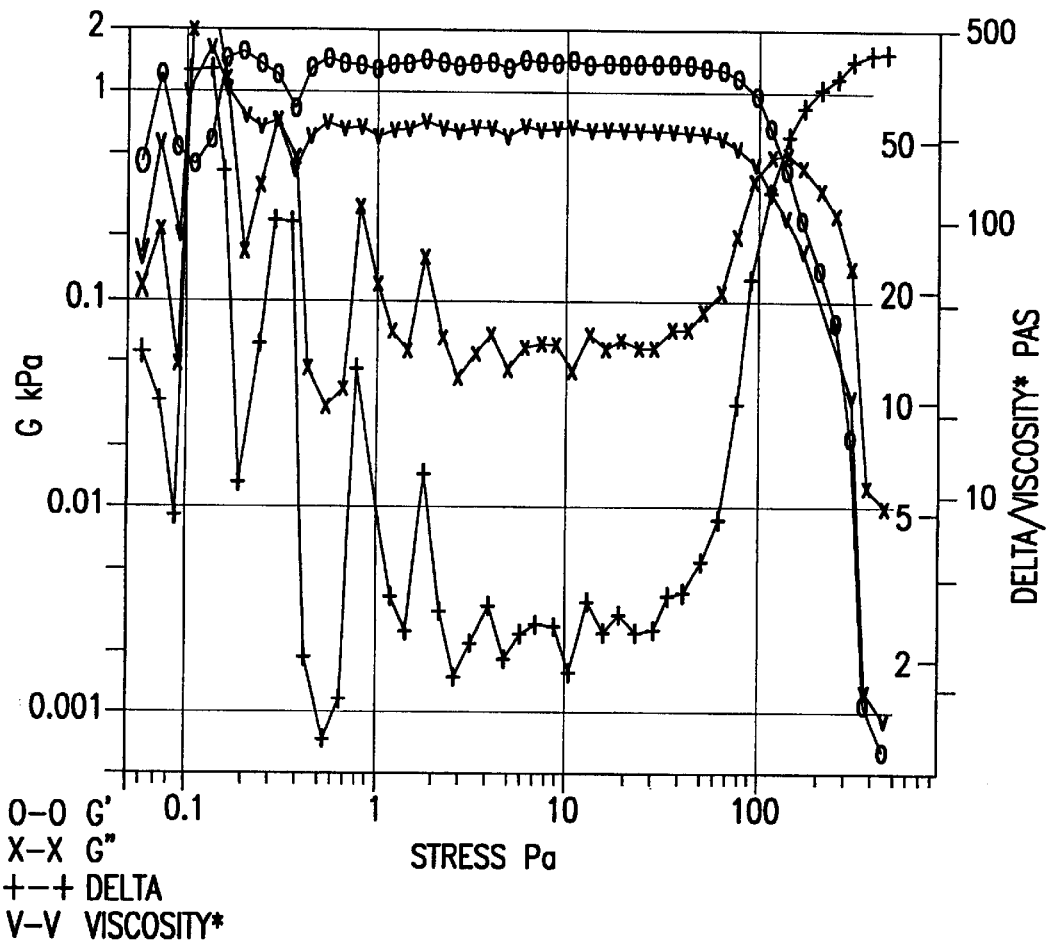
FIG. 5 shows the dynamic mechanical spectra of Example 7, Sample 5.
Figure 6:
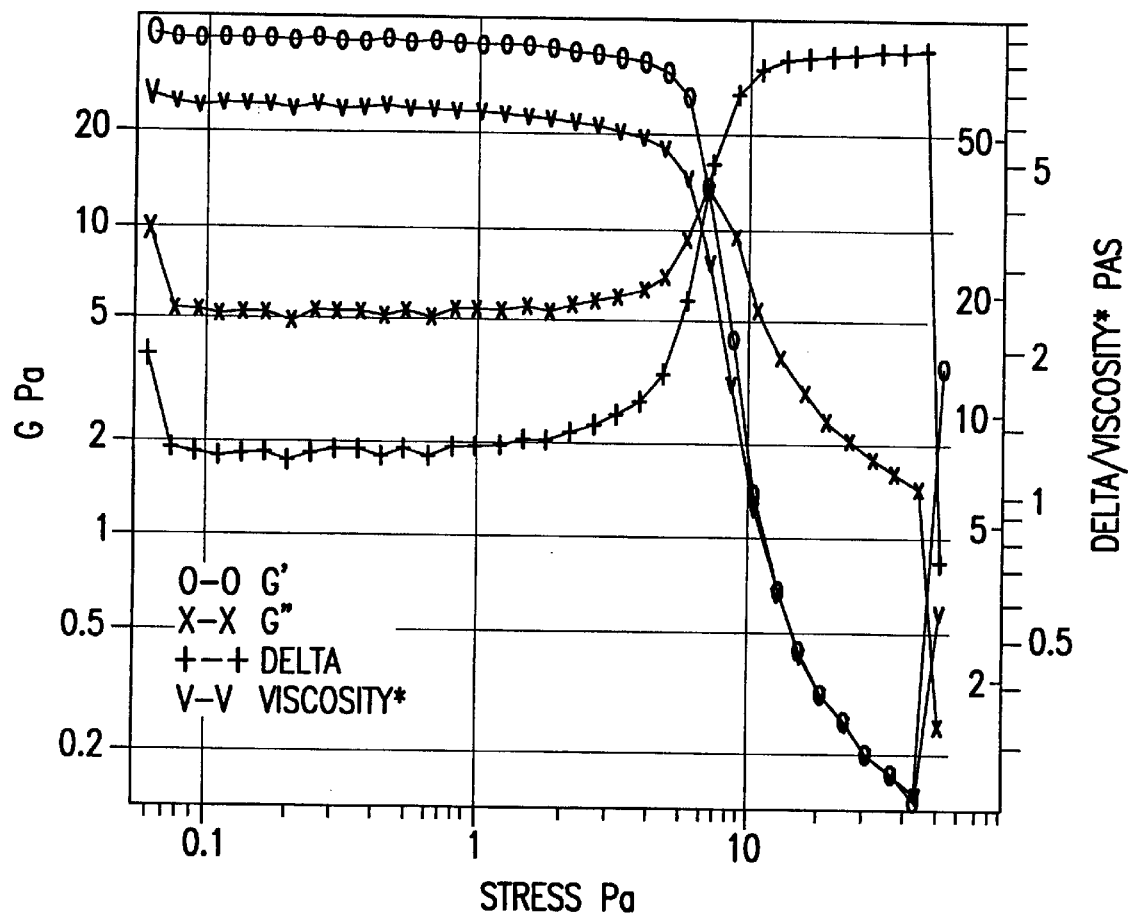
FIG. 6 shows the dynamic mechanical spectra of Example 13, Sample 1.
Figure 7:
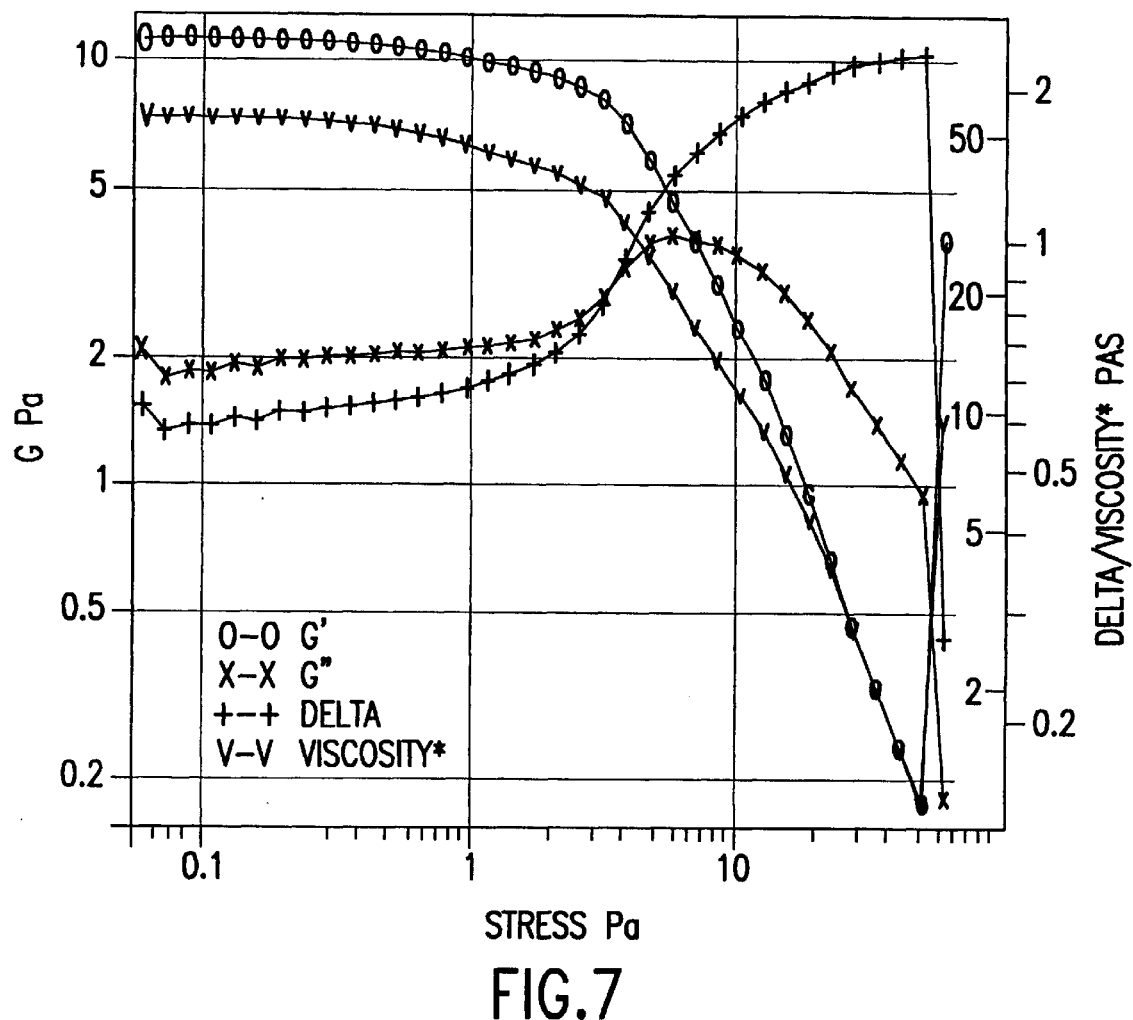
FIG. 7 shows the dynamic mechanical spectra of Example 13, Sample 2.
Figure 8:
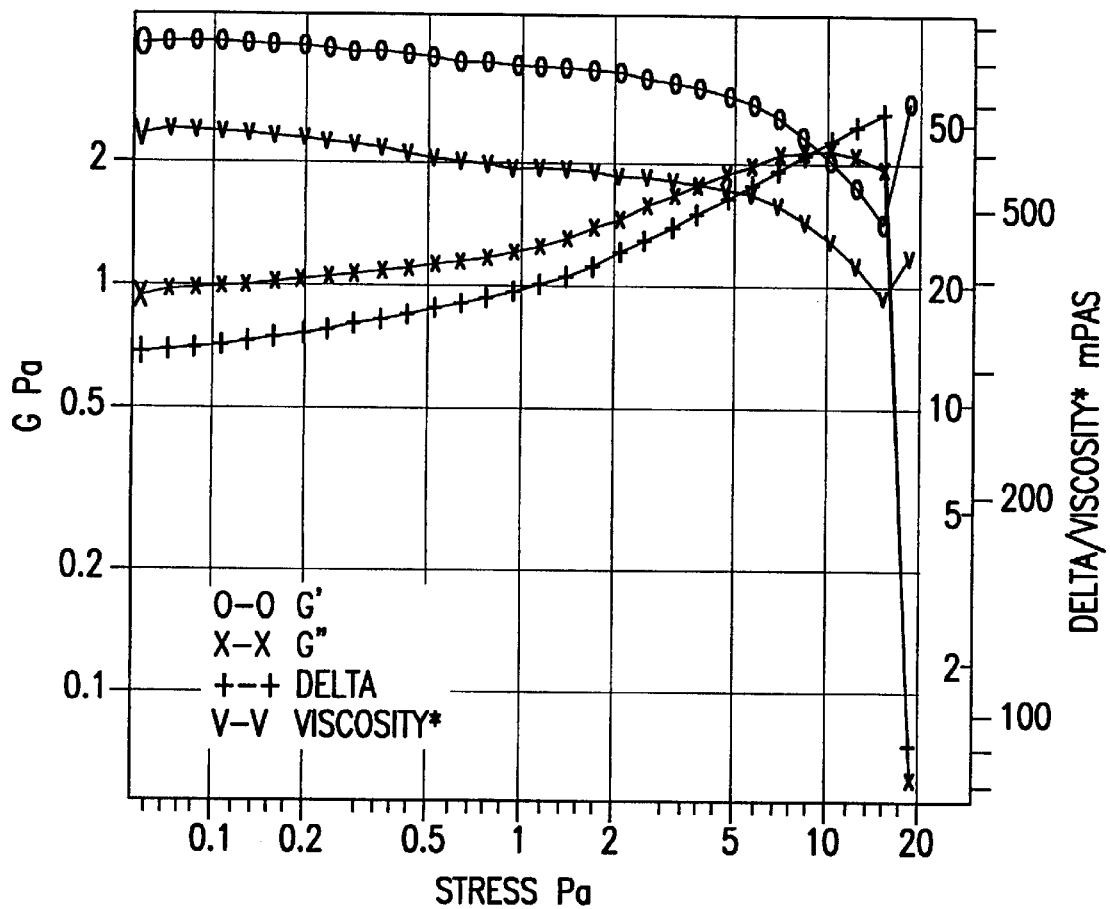
FIG. 8 shows the dynamic mechanical spectra of Example 13, Sample 3.

A copy of the dynamic mechanical spectra (obtained by the stress sweep test) of Sample 2 is given in FIG. 5.

EXAMPLE 7

Preparation of Ready-to-Gel Microfibrillated CMC

Gels were made as described in the slurry preparation and homogenization processing steps in Example 2 using CMC II as made in example 3 (DS about 0.16). The gels were then processed as follows (the following description pertains to Sample #1 in Table 11, and a similar procedure was used for all of the other samples):

Approximately 2800 ml of isopropyl alcohol was added to a grounded 12 quart stainless steel (SS) beaker. The IPA was stirred at the top speed of an overhead stirrer driven by house air. A SS cowls blade on a SS shaft was used to stir the IPA. about 1400 grams of 1% CMC II gel was slowly added to the stirring IPA. The material ratio was 2 ml IPA/1 gram gel. It took about 5 minutes to add the gel to the IPA. The beaker was covered with plastic film and the slurry was stirred for ten minutes.

When ten minutes had passed, the slurry was filtered through a synthetic straining cloth. The slurry was filtered using gravity. The slurry was covered with plastic film during the filtration to reduce IPA evaporation. Occasionally the gel on the cloth was stirred with a plastic spatula to help speed filtration. When it appeared that the filtration had gone about as far as it could, the wet cake was transferred back to the 12 quart SS beaker.

Approximately 2800 ml of fresh IPA was added to the beaker and the slurry was again stirred for ten more minutes with the cowls blade/air stirrer. The slurry was then filtered on a 20 cm Büchner funnel with #415 VWR filter paper. The wet cake was transferred to a glass crystallization dish. The dish and wet cake were placed into an 80° C. oven under vacuum overnight for drying. The sample was dried to constant weight. The solids were ground in a Waring Blender.

The dehydrated gels were examined by rehydration as follows: a premix of DI water and Germaben® II was prepared.

|  | Weight | Weight % |
|---|---|---|
| Deionized water | 788.00 grams | 99.49% |
| Germaben ® II biocide | 4.00 grams | 0.51% |

The water/Germaben® II solution was then weighed into a small Waring blender cup along with the Ready-to-gel dry CMC according to the recipes in Table 11. The blender cup was covered and the sample was mixed until it appeared to be homogeneous. The resulting gel was transferred to a glass jar. It was then shaken on a vortex mixer. Rheological testing was performed as described in example 2.

TABLE 11

Rheology of RTG CMC

| Sample | Wt. % water/ Germaben ® II | Wt % RTG CMC | Yield Stress (Pa) | G' @ 5.75 Pa (Pa) |
|---|---|---|---|---|
| 1 | 99.75 | 0.25 | 2.4 | 5.61 |
| 2 | 99.5 | 0.50 | 10.7 | 68.6 |
| 3 | 99.0 | 1.00 | 25.7 | 328 |
| 4 | 98.5 | 1.50 | 51.0 | 731 |
| 5 | 98.0 | 2.00 | 95.3 | 1400 |

A copy of the dynamic mechanical spectra (obtained by the stress sweep test) of Sample 1 through 5 are given in FIGS. 6 through 10, respectively.

EXAMPLE 8A

Acid Process for Preparation of Ready-to-Gel Microfibrillar CMC

A gel as prepared in example 3 was acidified using HCl to adjust the pH to about 2.7. The gel was centrifuged to remove about 60% of the water. The concentrated gel was then converted to RTG form by mixing with IPA equivalent to 2 times the weight of the gel, followed by filtration on a Büchner funnel and a second mix with another 2 times weight of IPA. The wet cake was dried in a vacuum oven.

The dried solids were rehydrated at 1% in water/Germaben® II biocide. A small amount of baking soda was added and the sample was mixed on the blender. Viscosity rose gradually with stirring and the sample became gel-like. The pH was about 6.9.

Rheological testing was performed as described in example 2. G' @ 5.75 Pa: 226 Pa, Yield Stress: 17.4 Pa. A copy of the dynamic mechanical spectra (obtained by the stress sweep test) is given in FIG. 11.

EXAMPLE 8B

Acid Process for Preparation of Ready-to-Gel Microfibrillar CMC

A second batch of gel as made in example 3 had its pH adjusted to about 2.7 with concentrated HCl. The sample was centrifuged and about 62% of the water was removed. About 97 g of concentrated gel was slurried with 150 ml IPA. The pH was adjusted to 7.0 during the stirring of the slurry by addition of a small amount of baking soda. The slurry was filtered on a Büchner funnel, and half of the wet cake (Sample A) was weighed into a crystallization dish for drying. For Sample B, the other half of the wet cake was reslurried in about 75 ml IPA. This wet cake was filtered on a Büchner funnel and was pressed with rubber dam to remove as much IPA as possible. Both wet cakes were dried to constant weight under vacuum, and the solids were ground up in a Waring blender.

Sample A was mixed with water for a total solids level of 1%, and gelled quickly. The pH was about 5.8. Sample B gelled quickly when stirred in water at a solids level of 1%.

Rheological testing was performed as described in example 2. Sample A: G' @ 5.75 Pa: 471 Pa, Yield Stress: 34.0 Pa. A copy of the dynamic mechanical spectra (obtained by the stress sweep test) is given in FIG. 12. Sample B: G' @ 5.75 Pa: 403 Pa, Yield Stress: 35.7 Pa. A copy of the dynamic mechanical spectra (obtained by the stress sweep test) is given in FIG. 13.

EXAMPLE 9

Derivatization of Microfibrillar Cellulose

Isopropanol (602.8 g) and DI water (86.4 g) were charged to a nitrogen sparged, jacketed resin kettle equipped with an air driven stirrer, stainless steel agitator, two pressure equalizing addition funnels, a reflux condenser, nitrogen inlet, vacuum line and thermocouple. Microfibrillated cellulose of Example 1 was vacuum filtered with a sintered glass funnel and a rubber dam. The wetcake was slurried in 565 g of 80% isopropanol (IPA) for 15 minutes using an air driven stirrer and a grounded stainless steel beaker and then aspirator vacuum filtered with a sintered glass funnel and a rubber dam. This was repeated two more times.

The wetcake obtained from the previous three washes was slurried in 1000 g of pure IPA using an air driven stirrer and a grounded stainless steel beaker for 15 minutes to dehydrate and then aspirator vacuum filtered with a sintered glass funnel and rubber dam. The resulting wet cake, comprised of 36 g microfibrillated cellulose, 228 g IPA, and 36 g DI water was added to the reactor, the mixture slurry was agitated for 10 minutes, after which the mixture was nitrogen sparged for 1 hour while cooling the slurry temperature to 15° C. The reactor was inerted. Aqueous 50% NaOH (10.52 g) was slowly added to the reactor maintaining the mixture slurry's temperature at about 15° C. The slurry was agitated for 1 hour after completion of caustic addition. Aqueous monochloroacetic acid (7.26 g of 80% aq MCA) was slowly added to the reactor by funnel while maintaining reaction slurry temperature at about 15° C. After MCA addition, the reaction slurry was heated to about 70° C. and held for 1.5 hours. The reaction slurry was cooled down to below 30° C. and then aspirator vacuum filtered with a sintered glass funnel and a rubber dam. The wetcake was slurried in 565 g of 80% methanol for 15 minutes using an air driven stirrer and a grounded stainless steel beaker and then aspirator vacuum filtered with a sintered glass funnel and a rubber dam. This was repeated two more times. The wetcake obtained from the previous three washes was slurried in 1000 g of pure methanol using an air driven stirrer and a grounded stainless steel beaker for 15 minutes to dehydrate and then aspirator vacuum filtered with a sintered glass funnel and rubber dam. The final wetcake was dried in the fluidized bed dryer for 35 minutes (air-dry for 5 minutes, heat-dry at 50° C. for 10 minutes and heat-dry at 70° C. for an additional 20 minutes). The product was ground using the Retsch mill with a 1 mm screen. DS of the resulting material was 0.14.

A 1% aqueous suspension of the product was mixed in a Waring blender for 15 minutes. This produced a viscous suspension which did not settle with time. Slurry preparation: Same as in example 2. Homogenization was performed as in example 2, except where otherwise stated, and rheological testing was performed as in example 2. Yield Stress: 5.75 Pa, G' @ 5.75 Pa: 363 Pa. A copy of the dynamic mechanical spectra (obtained by the stress sweep test) is given in FIG. 14.

EXAMPLE 10

Alternative Cellulose

CMC was produced as in example 3 using the cellulose source and recipe in Table 12.

TABLE 12

| | | Alternative Cellulose Recipe (all weights in grams) | | | | | |
|---|---|---|---|---|---|---|---|
| Sample | Cellulose Source | Wt Cellulose (dry wt. basis) | Wt. IPA | Wt. $H_2O$ | Wt. 50% NaOH (aq) | Wt. 80% MCA (aq) | DS |
| 1 | Avicel ® pH-101NF (−90) | 62.01 | 750 | 113.49 | 19.00 | 13.11 | 0.16 |
| 2 | Solka ® Floc (1) | 61.23 | 750 | 114.27 | 19.00 | 13.11 | 0.19 |
| 3 | CTMP (2) | 54.5 | 750 | 121 | 19.00 | 13.11 | 0.22 |

(1) Solka Floc (grade 300 FCC) obtained from Fiber Sales & Development Corp., Urbana, Ohio.
(2) Bleached CTMP (Chemical Thermomechanical Pulp) Fluff obtained from SCA Graphic Sundsvall AB, Timra, Sweden Slurry preparation of the Solka Floc sample (Sample 2) was prepared as in Example 2. Homogenizer processing was performed as in Example 2, and rheological testing was performed as in Example 2.

TABLE 13

Rheology

| Sample | Cellulose Source | DS of CMC | Yield Stress[1] (Pa) | G' @ 5.75 Pa (Pa) |
|---|---|---|---|---|
| 2 | Solka Floc | 0.19 | 22.4 | 141 |

[1]From yield stress test/from stress sweep test.

A copy of the dynamic mechanical spectra of sample 2 is given in FIG. 15.

EXAMPLE 11

Microfibrillation of CMC with Impingement Mixer

The samples used were 0.5%, 1.0% and 1.5% suspensions of low DS CMC prepared as in Example 3. Each slurry weighed a total of 100 grams. No Germaben® II biocide was used in the samples processed in the impingement mixer. The slurries were prepared by weighing the components into four ounce glass jars. The jars were capped and shaken to wet and disperse the CMC solids.

|  | Sample #1 (0.5%) | Sample #2 (1.0%) | Sample #3 (1.5%) |
|---|---|---|---|
| CMC | 0.50 grams | 1.0 grams | 1.5 grams |
| DI water | 99.5 grams | 99.0 grams | 98.5 grams |

A Microfluidics Corporation Model M110 Series impingement mixer was flushed with DI water prior to use. The pressure was adjusted to the desired setting as the water was pumped. The impingement mixer was run such that the DI water was pumped until it was just at the bottom of the charge funnel. A heating bath used to control the temperature of the impingement mixer piping was set at 50° C.

The sample jar was shaken again just before charging the sample funnel. The sample was charged into the funnel. An electric overhead stirrer was in the sample funnel. This was turned on to help keep the CMC homogeneously suspended. After the first pass, the stirrer is not needed. The sample was pumped through the microfluidizer and out into a collection jar. The material initially collected which contains the initial DI residue was discarded. Processing was then continued until the entire sample had been processed for 1 pass through the equipment.

The 0.5% solids gel was processed at 6000 psi for 4 passes. The 1.0% solids gel was processed under the same conditions. The 1.5% solids gel was processed at 6000 psi for just 3 passes.

TABLE 14

Rheology of Impingement Mixer Microfibrillated CMC

| Sample | Cellulose Length | DS of CMC | Yield Stress (Pa) | G' @ 5.75 Pa (Pa) | G' @ 25° C./50° C. (Pa) |
|---|---|---|---|---|---|
| 1 | ~400 μm (0.5% solids gel) | 0.17 | 4.82 | 79.3 | 97/109 |
| 2 | ~400 μm (1.0% solids gel) | 0.17 | Not Tested | 270 | 222/242 |
| 3 | ~400 μm (1.5% solids gel) | 0.17 | Not Tested | 522 | 363/434 |

A copy of the dynamic mechanical spectra (obtained by the stress sweep test) of Samples 1 through 3 are given in FIGS. 16 through 18.

EXAMPLE 12

Microfibrillated Hydrophobically Modified Carboxymethyl Cellulose (HMCMC)

Tert-butyl alcohol (TBA, 750 g) and Hercules CMC 7H (DS of about 0.7, 100 g) were charged to a nitrogen sparged, jacketed resin kettle equipped with an air driven stirrer, stainless steel agitator, two pressure equalizing addition funnels, a reflux condenser, nitrogen inlet, vacuum line and thermocouple. The mixture was nitrogen sparged for 1 hour at 25 E C.

Aqueous NaOH (54 g of 7.5% NaOH) was slowly added to the reactor maintaining the mixture slurry's temperature at about 25° C. The slurry cooled to about 15E C and was agitated for 1 hour at about 15E C. A 50% solution of cetyl glycidal ether (40 g of solution) was slowly added to the reactor by addition funnel while maintaining reaction slurry temperature at about 15° C. The reaction slurry was heated to about 80° C. and held for 3.25 hours. The reaction slurry was cooled down to about 50° C. and 9 g of 70% nitric acid was added. The mixture was cooled to about 30E C and then aspirator vacuum filtered with a sintered glass funnel and a rubber dam. The wetcake was slurried in 1000 g of 85% acetone for 15 minutes using an air driven stirrer and a grounded stainless steel beaker and then aspirator vacuum filtered with a sintered glass funnel and a rubber dam. This was repeated two additional times. The wetcake obtained from the previous three washes was slurried in 1000 g of 100% acetone using an air driven stirrer and a grounded stainless steel beaker for 15 minutes and then aspirator vacuum filtered with a sintered glass funnel and rubber dam. The final wetcake was dried in the fluidized bed dryer for 35 minutes. (Air-dry for 5 minutes, heat-dry at 50° C. for 10 minutes and heat-dry at 70° C. for an additional 20 minutes) The product was ground using the Retsch mill with a 1 mm screen. The cetyl content of the resulting product was # 0.03 wt. %. Slurry preparation, homogenizer processing, and Theological testing were performed as described in example 2. G' @ 5.75 Pa: 319 Pa, Yield Stress: 14 Pa. A copy of the dynamic mechanical spectra (obtained by the stress sweep test) is given in FIG. 19. While the use of hydrophobically modified derivatized microfibrillar cellulose has been demonstrated herein by a particular example, for purposes of the present invention a derivatized microfibrillar cellulose may be hydrophobically modified by carbon groups having from about 4 to about 30 carbons.

EXAMPLE 13

Microfibrillated Hydroxyethylcellulose (HEC)

Sulfate wood pulp, tert-butyl alcohol (TBA), acetone, isopropanol (IPA) and DI water were charged to a nitrogen sparged, agitated Chemco reactor (3 pint reactor, Chemco, Tulsa, Okla.). The reactor was inerted with nitrogen and the reaction slurry temperature was adjusted to 20E C. Aqueous NaOH (50% NaOH) was added to the reactor and the mixture was agitated for 45 minutes at 20 E C. Ethylene oxide (EO) was charged to the reactor over a period of about 5 minutes, maintaining the reaction slurry at 20E C. After EO addition, the reaction slurry was heated to 50E C and maintained at 50E C with agitation for about 45 minutes. The reaction slurry was then heated to about 90E C and maintained at 90E C with agitation for 30 minutes. The reaction slurry was cooled to about 50E C and 70% nitric acid was added. The reaction slurry was cooled to below 30E C and then aspirator vacuum filtered with a sintered glass funnel and a rubber dam. The wetcake was slurried in 600 g of 80% acetone for 15 minutes using an air driven stirrer and a grounded stainless steel beaker and then aspirator vacuum filtered with a sintered glass funnel and a rubber dam. This was repeated two additional times. The wetcake obtained from the previous three washes was slurried in 600 g of 100% acetone water using an air driven stirrer and a grounded stainless steel beaker for 15 minutes and then aspirator vacuum filtered with a sintered glass funnel and rubber dam. The final wetcake was dried in the fluidized bed dryer for 35 minutes (air-dry for 5 minutes, heat-dry at 50° C. for 10 minutes and heat-dry at 70° C. for an additional 20 minutes). The product was ground using the Retsch mill with a 1 mm screen.

TABLE 15

HEC Recipes
(all weights in grams)

| Sample # | Cellulose | TBA | IPA | Acetone | H$_2$O | 50% NaOH | EO | 70% Nitric Acid | MS |
|---|---|---|---|---|---|---|---|---|---|
| 1 | 46.0 | 517.8 | 8.6 | 7.9 | 63.5 | 13.0 | 16.1 | 14.6 | 0.7 |
| 2 | 49.77 | 517.8 | 8.6 | 7.9 | 59.73 | 12.7 | 10.6 | 14.6 | 0.8 |
| 3 | 49.77 | 517.8 | 8.6 | 7.9 | 59.73 | 13.0 | 19.5 | 14.6 | 1.3 |

Slurry preparation and homogenizer processing were performed as in example 2, except that fewer passes were required to process to a gel.

TABLE 16

Rheology of Microfibrillated HEC

| Sample | MS of HEC | Yield Stress (Pa) | G' @ 5.75 Pa (Pa) |
|---|---|---|---|
| 1 | 0.7 | 1.66 | 43.6 |
| 2 | 0.8 | 3.65 | 10.3 |
| 3 | 1.3 | 2.98 | 2.96 |

A copy of the dynamic mechanical spectra (obtained by the stress sweep test) of Samples 1 though 3 are given in FIGS. 20 through 22.

Drainage Aids in Paper Manufacture: the following examples demonstrate the effectiveness of derivatized microfibrillar polysaccharide as a drainage-improvement aid.

Drainage measurements were performed on a Canadian Standard Freeness (CSF) tester, using a bleached kraft pulp consisting of 70% hardwood and 30% softwood. All freeness testing was performed in hard water having a pH of 7.95–8.05, alkalinity of 50 ppm (as calcium carbonate), and hardness of 100 ppm (as calcium carbonate) using TAPPI method T 227 om-92. A pulp consistency of 0.3% was used. Higher CSF values indicate better (faster) drainage.

The following results were obtained using RTG microfibrillated CMC prepared in example 7, which has a degree of substitution of about 0.17 charge group per anhydroglucose unit. All loadings are calculated as percent of additive (dry basis) relative to pulp.

EXAMPLE 14

RTG CMC Sample Material Alone

| % RTG CMC Material (based on pulp) | CSF |
|---|---|
| 0 | 210 |
| 0.025 | 274 |
| 0.050 | 285 |
| 0.100 | 315 |
| 0.200 | 317 |

EXAMPLE 15

RTG CMC Sample Material and Hercules Reten® 1232 (R-1232)

| | CSF VALUES | |
|---|---|---|
| % RTG Material (based on pulp) | 0.1% R-1232 | 0.2% R-1232 |
| 0 | 380 | 462 |
| 0.1 | 485 | 591 |
| 0.2 | 526 | 608 |
| 0.4 | 587 | 637 |
| 0.6 | 572 | 671 |

EXAMPLE 16

RTG CMC Sample Material and Hercules Kymene® 557H resin (K-557H)

A constant 2:1 ratio of K-557H to material was employed. (Kymene is a registered trademark of Hercules Incorporated.) Two different starting pulps were used, one with a relatively high freeness, and one relatively low.

| % RTG Material (based on pulp) | % K-557H | Pulp 1 CSF | Pulp 2 CSF |
|---|---|---|---|
| 0 | 0 | 184 | 413 |
| 0.1 | 0.2 | 281 | 531 |
| 0.2 | 0.4 | 321 | 565 |
| 0.4 | 0.8 | 382 | 574 |

EXAMPLE 17

RTG CMC Material and Hercules Kymene 450 resin (K-450)

A constant 2:1 ratio of K-450 to sample material was employed. Two different starting pulps were used, one with a relatively high freeness, and one relatively low.

| % RTG Material (based on pulp) | % K-450 | Pulp 1 CSF | Pulp 2 CSF |
|---|---|---|---|
| 0 | 0 | 184 | 413 |
| 0.1 | 0.2 | 285 | 536 |
| 0.2 | 0.4 | 335 | 546 |
| 0.4 | 0.8 | 357 | 562 |

As with ordinary CMC, the sample material extends the wet and dry strength activity of additives such as Hercules Kymene 557H or Kymene 450 resin. Thus an advantage of the use of the sample material is the provision of a combined wet strength/dry strength/drainage/retention aid.

Use in paper sizing compositions: the following examples relate to use CMC II as made in example 3 having a DS of about 0.15 in connection with compositions used in paper sizing.

EXAMPLE 18

A 600 ml beaker was used to combine 66.0 grams of Precis® 787 ketene dimer (available from Hercules Incorporated, Wilmington, Del.; Precis is a registered trademark of Hercules Incorporated), 1.5 g of CMC II (as made in example 3, DS about 0.15), and 232.5 grams of DI water. The pre-mix was dispersed by stirring for two minutes using a Tekmar Ultra-turax SD45 rotor-stator high shear mixer (Tekmar Company, Cincinnati, Ohio) at a power setting of 50. This pre-mix was then quickly poured into the feed chamber of the impingement mixer. With mechanical stirring at about 250 RPM, premix was passed through the impingement mixer with its pressure set at 5000 psi. The emulsion was collected and a second pass was made. The second pass product was collected in a clean jar, a stir bar was added, the jar was capped, and then cooled in a 5 to 15° C. water bath.

EXAMPLE 19

Same as Example 18, using 66.0 g Precis ketene dimer, 1.5 g of the sample material, 66.0 g of 50% aluminum sulfate (18H$_2$O) solution in water, and 166.5 g DI water.

EXAMPLE 20

Same as Example 18, using 66.0 g Precis ketene dimer; 1.5 g of the sample material; 132.0 g of a solution containing 25% (wt) aluminum sulfate (18H$_2$O), deionized water, and sufficient alkalinity to raise the pH to 4.0; and 100.5 g DI water.

EXAMPLE 21

Same as Example 18, using 66.0 g Precis ketene dimer; 75.0 g of a 2% solution of CMC 7M (DS of 0.7) (Hercules Incorporated, Wilmington Del.) in deionized water; and 132.0 g of a solution containing 25% (wt) aluminum sulfate (18H$_2$O), deionized water, and sufficient alkalinity to raise the pH to 4.0; and 27.0 g DI water.

EXAMPLE 22

3.0 g of CMC II (as made in example 3, DS about 0.15) were dispersed in 465 g DI water for 5 minutes using the high shear mixer at a power setting of 50, then given three passes through the impingement mixer at 5000 psi. As in Example 18, 66.0 g Precis ketene dimer were combined with 234.0 g of the sample material in DI water gel, stirred using the high shear mixer at a power setting of 50, then given two passes through the impingement mixer at 5000 psi and cooled.

EXAMPLE 23

4.0 g of CMC II (as made in example 3, DS about 0.15) was dispersed in 400 g DI water for 5 minutes using the high shear mixer at a power setting of 50, then given three passes through the Microfluidizer at 5000 psi to give a gel.

In an 8 ounce wide mouth jar, 176.0 grams of Precis 787 ketene dimer and 224.0 grams of DI water were combined. The pre-mix was sheared in the high shear mixer for 5 minutes at a power setting of 50, then quickly poured into the feed chamber of the impingement mixer. With mechanical stirring at about 250 RPM, the premix was passed twice through the impingement mixer set at 5000 psi 150.0 g of the gel made above was combined with 150.0 g Precis ketene dimer 44% emulsion, and stirred 5 minutes using the high shear mixer at a power setting of 50.

EXAMPLE 24

In an 8 ounce wide mouth jar, 66.0 grams of Precis 787 ketene dimer, 1.5 g of pre-sheared, solvent exchange dried material as made in Example 7 (DS of about 0.16), and 232.5 grams of DI water were combined. The pre-mix was sheared in the high shear mixer for 5 minutes at a power setting of 50, then quickly poured into the feed chamber of the impingement mixer. With mechanical stirring at about 250 RPM, the premix was passed through the impingement mixer at 5000 psi. The emulsion was collected and a second pass was made. The second pass product was collected in a clean jar, a stir bar was added, and the jar was capped and cooled in a 5 to 15° C. water bath.

The following pages provide testing results for the sample emulsions using TAPPI Standard Method T560:

TABLE 17

Surface Sizing of Example 18 through Example 24 Size Emulsions
(formulation weight in grams)

|  |  |  |  |  | (Pre-shear) | | |
|---|---|---|---|---|---|---|---|
|  |  |  |  |  | (MF gel) | (MF gel) | (RTG) |
| Example # | 18 | 19[1] | 20 | 21 | 22 | 23[1] | 24 |
|---|---|---|---|---|---|---|---|
| Precis 787 | 66.00 | 66.00 | 66.00 | 66.00 | 66.00 | 66.00 | 66.00 |
| Microfibrillated CMC | 1.50 | 1.50 | 1.50 |  | 1.50 | 1.50 | 1.50 |
| 50% Alum |  | 66.00 |  |  |  |  |  |
| 25% Alum pH 4.0 |  |  | 132.00 | 132.00 |  |  |  |
| 2% CMC 7M |  |  |  | 75.00 |  |  |  |
| DI Water | 232.50 | 166.50 | 100.50 | 27.00 | 232.50 | 232.50 | 232.50 |
| Total | 300.0 | 300.0 | 300.0 | 300.0 | 300.0 | 300.0 | 300.0 |
| Rotor-stator Shearing | 2 min.@50 | 2 min.@50 | 2 min.@50 | 2 min.@50 | 2 min.@50 | 2 min.@50 | 5 min.@50 |
| Impingement Mixer Shearing | 2X@ 5 kpsi | 2X@ 5 kpsi | 2X@ 5 kpsi | 2X@ 5 kpsi | 2X@ 5 kpsi |  | 2X@ 5 kpsi |
| Rotor-stator Gel Shearing |  |  |  |  | 5 min.@50 | 5 min.@50 |  |
| Impingement Mixer Gel Shearing |  |  |  |  | 3X@ 5 kpsi | 3X@ 5 kpsi |  |

[1]Examples 19 and 23 gave emulsions which broke overnight and were not suitable for surface sizing the next day. The failure of Example 19 is most likely due to low pH resulting from the presence of the 50% alum, and can be corrected by raising the pH of the alum. Without being bound by any particular theory, it is known that aluminum can appear in a polymeric form, and so may form a co-acervate, at higher pH. In general, the pH of the alum, poly-aluminum chloride, or other aluminum salts should preferably be as near as possible to the pKa of the derivatized microfibrillar cellulose. Thus, in Example 18 the addition of low pH 50% alum solution gave an emulsion with poor stability, while similar recipes in Examples 18 and 20, made without alum or with alum whose pH had been raised to pH 4.0, gave good emulsions. In Example 23, adding the microfibrillated gel without a second impingement mixer shearing as in Example 22 gave an emulsion which was not stable overnight, and thus could not be size tested the next day.

The emulsions from Examples 18, 20, 21, 23, and 24 were then tested in sizing compositions, and the results are shown in Chart 1. The procedure used to obtain this data was as follows: all samples were made with 5% (wt.) D-150 starch (Grain Processing Corp., Muscatine, Iowa). Five pieces of paper and a wet pick-up sheet for each run were size pressed using a wet nip size press. Each sheet was dry pressed with a drum dryer at 220° F.±5° F. for 20 seconds. The weight of wet the pick-up sheet was determined before and after the size press to give wet pick-up percent. Hercules Size Testing (HST) was performed on each paper sheet (5 per run) utilizing TAPPI procedure T560.

EXAMPLES 25–27

A series of emulsions was made using Aquapel® 364 sizing agent rather than Precis ketene dimer as the size, with the formulations shown in Table 18. In each case the sample was sonicated on a Branson 350 Ultrasonicator at a power setting of 6. Samples of fine paper were made on a continuous Fourdrinier-type machine, using the emulsions and sizing tested after 100 hours natural aging using a standard HST ink resistance test (TAPPI Method T-530) using a 1% formic acid ink. Chart 2 shows the HST sizing results, which show the samples to be at least as good as or better than three commercial controls using Hercon® paper sizing agent.

CHART 1

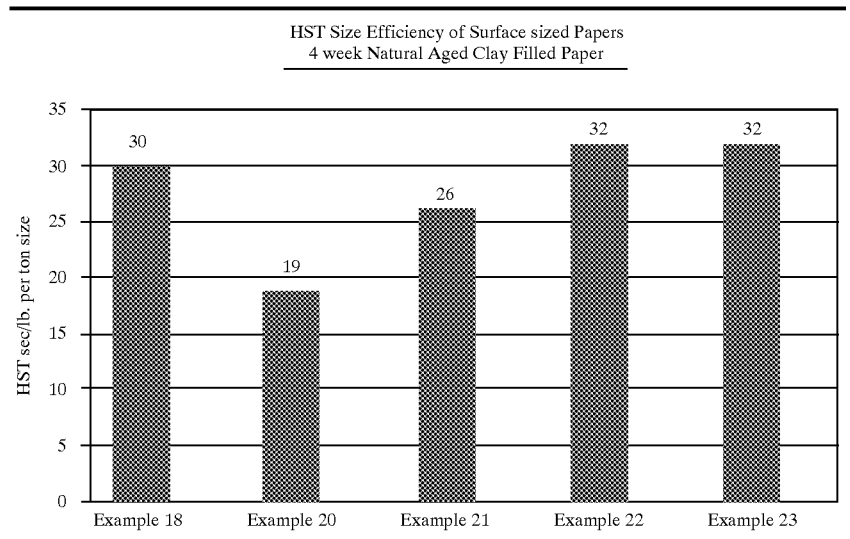

HST Size Efficiency of Surface sized Papers
4 week Natural Aged Clay Filled Paper

TABLE 18

|  | Example 25 | Example 26 | Example 27 |
|---|---|---|---|
| Aquapel 364 (1) | 10 | 10 | 10 |
| Carrageenan 2% (2) | 50 | | |
| CMCII (prepared in Example 3, DS about 0.15) | | 1 | |
| Ambergum ® CMC 2% (3) | | | 50 |
| pH 4 Alum | 20 | 20 | 20 |
| Reten ® 203 20% (4) | 5 | 5 | 5 |
| Diocide AMA 415 | 0.02 | 0.02 | 0.02 |
| Water | 14.98 | 63.98 | 14.98 |

(1) Aquapel 364 Ketene Dimer sizing agent - Hercules Incorporated
(2) Carrageenan - GenuGel ® Carrageenan Type LC-5, Hercules Incorporated
(3) Ambergum - Type 99-3021, Hercules Incorporated
(4) Reten 203 - Cationic resin, Hercules Incorporated
(Ambergum, Aquapel, Hercon, Genugel, and Reten are registered trademarks of Hercules Incorporated)

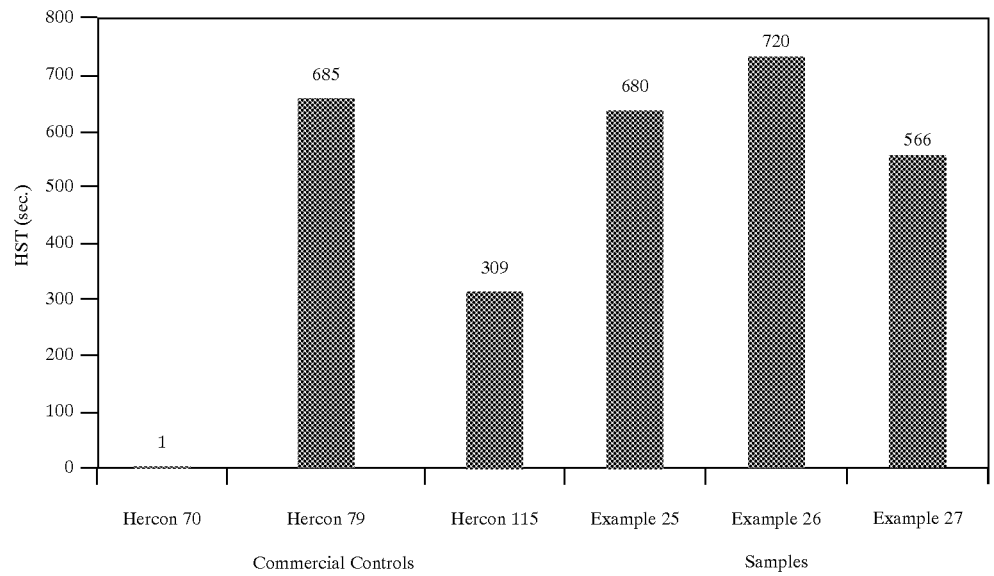

CHART 2

AKD Emulsions in Unfilled Fine Paper
0.06% Size (wt) based on pulp, 4 day Natural Aged Commercial Controls: Hercon 70 (1), Hercon 79 (685), Hercon 115 (309)
Samples: Example 25 (680), Example 26 (720), Example 27 (566)

Papermaking

The paper used in the sizing examples was made at pH 7 from a 75:25 blend of hardwood and softwood pulps beaten to a Canadian standard freeness of 525 and formed into sheets having a basis weight of 65.1 g/m². Hercon 70, Hercon 79, and Hercon 115 sizing agents were all added at 0.06%, based on the pulp (corresponding to 1.2 pounds per ton). Laboratory water was used, having a hardness of 50 ppm, an alkalinity of 25 ppm, and a pH of 8.1–8.4.

Use in food and personal care compositions: the following examples relate to the use or derivatized microfibrillar polysaccharides in food and personal care products.

EXAMPLE 28

Use as Fat Replacer, Viscosifier in Food Applications

| | Fat Free Mayonnaise Model System | | |
|---|---|---|---|
| Ingredients (wt. %) | 1 | 2 | 3 |
| RTG Microfibrillated CMC | 0.8 | | |
| Microfibrillated CMC | | 0.8 | |
| water | 76.2 | 76.2 | 77.0 |
| starch (Pureflo)* | 4.0 | 4.0 | 4.0 |
| maltodextrin | 10.0 | 10.0 | 10.0 |
| salt | 2.0 | 2.0 | 2.0 |
| vinegar (12% acetic acid) | 4.0 | 4.0 | 4.0 |
| egg yolk | 3.0 | 3.0 | 3.0 |
| viscosity (cps) | 42000 | 45000 | 6000 |

*marketed by National Starch and Chemical Co.

Procedure 1: RTG Microfibrillated CMC prepared in example 7 above (DS about 0.16) was dispersed in water with agitation. Starch and maltodextrin were added with agitation.

The mixture was heated to 80°–90° C. followed by cooling to 15°–20° C. Egg yolk then vinegar were added. The product was then mixed by means of a colloid mill. This mixing consists of one pass through a Greerco colloid mill model W250V-B (Greerco Corp., Hudson, N.H.) with an emulsion rotor and stator at a 0.001 inch gap setting. The texture of this product is then evaluated after 24 hours.

Procedure 2: to a 1% microfibrillated CMC gel as made in example 3 above (DS about 0.16) the balance of the water was added Starch and maltodextrin were then added with agitation. The mixture was heated to 80°–90° C. followed by cooling to 15°–20° C. Egg yolk then vinegar were added. The product was then mixed by means of a colloid mill. The texture of this product is then evaluated after 24 hours.

Procedure 3: starch and maltodextrin were added to water with agitation. The mixture was heated to 80°–90° C. followed by cooling to 15°–20° C. Egg yolk then vinegar were added. The product is then mixed by means of a colloid mill. The texture of this product is then evaluated after 24 hours.

Evaluation: viscosity was measured with a Brookfield (Model DV-II+), 20° C., helipath, 5 rpm spindle C, program S93.

The appearance of the product containing either RTG Microfibrillated CMC or Microfibrillated CMC is that of a gel that holds its shape for a period of time when cut and does not synerese. When a portion of the product is lifted with a spoon or spatula, it does not appear to have stringiness of excessive tackiness; the texture is described as short. These are subjective textural features similar to that of reduced fat spoonable dressings and mayonnaises.

EXAMPLE 29

Use in Personal Care Products

| | Moisturizing Lotion | |
|---|---|---|
| Phase | Ingredient | Wt % |
| A | DI water | 81.85 |
| | Hydrophobe Modified Hydroxyethyl Cellulose (Natrosol ® Plus 330, Hercules Incorporated) | 0.24 |
| | Glycerin | 2.00 |
| | Disodium ethylene diamine tetraacetic acid | 0.05 |
| B | Petrolatum | 5.00 |
| | Mineral Oil | 3.00 |
| | Glycol Stearate | 2.00 |
| | Isostearyl Benzoate | 2.00 |
| | Parraffin | 2.00 |
| | Dimethicone | 0.50 |
| | RTG microfibrillar CMC as in example 7 (DS about 0.16) | 0.36 |
| C | Germaben ® II (preservative) | 1.00 |

Procedure: the Part A ingredients were combined, mixed until the water-soluble polymer dissolved, and heated to 60–65° C. All Part B ingredients were combined except the microfibrillar CMC, and heated to 60–65° C. until homogeneous. The RTG microfibrillar CMC was then dispersed into part B, and part B was added to part A with vigorous agitation, which was continued until the mixture was smooth and homogeneous. It was then cooled to 30° C., and part C was added.

| Properties | |
|---|---|
| pH | 5.7 |
| Viscosity* (cP) at 25° C. | 16,600 |
| Appearance | Milky-white emulsion |
| Stability | >5 weeks at 50° C. |

*Complex viscosity in linear viscoelastic regime was measured with a Bohlin controlled stress rheometer.

This example demonstrates the ability of the RTG CMC material to stabilize an oil in water emulsion, performing a role typically performed by surfactant/cosurfactant network forming systems.

| | Night Cream | |
|---|---|---|
| Phase | Ingredient | Wt % |
| A | DI water | 78.3 |
| | Glycerin | 2.00 |
| | Germaben ® II (preservative) | 0.50 |
| | Hydrophobically Modified Hydroxyethyl Cellulose (Natrosol ® Plus 330, Hercules Incorporated) | 0.72 |
| B | Avocado Oil | 4.00 |
| | Isostearyl Isostearate | 4.00 |
| | Octyl Stearate | 3.00 |
| | Isopropyl Myristate | 3.00 |
| | Propylene Glycol Isostearate | 4.00 |
| | RTG Microfibrillar CMC as in example 7 (DS about 0.16) | 0.48 |

Procedure: the ingredients for part A were combined and mixed until the water-soluble polymer dissolved. The ingredients for part B were then combined, and part B was added to part A with vigorous agitation, which was continued until the mixture was smooth and homogeneous.

| Properties | |
|---|---|
| pH | 6.0 |
| Viscosity* (cP) at 25° C. | 30,200 |
| Appearance | Creamy white emulsion |
| Stability | >5 weeks at 50° C. |

*Complex viscosity in linear viscoelastic regime was measured with a Bohlin rheometer.

This example demonstrates the ability of the RTG CMC material to stabilize an oil in water emulsion, performing a role typically performed by surfactant/cosurfactant network-forming systems. The RTG CMC also is processed at room temperature, while typical surfactant/cosurfactant systems require heat.

| | Alpha-Hydroxy Acid Anti-Age Cream | |
|---|---|---|
| Phase | Ingredient | Wt % |
| A | DI water | 71.9 |
| | Glycerin | 5.4 |
| B | Cetyl Alcohol | 3.2 |
| | Glyceryl Stearate and PEG-100 Stearate (Arlacel 165, ICI) | 4.8 |
| | Stearic Acid | 1.6 |

Alpha-Hydroxy Acid Anti-Age Cream

| Phase | Ingredient | Wt % |
|---|---|---|
|   | Isopropyl Palmitate | 4.8 |
|   | Mineral Oil and Lanolin Alcohol (Amerchol L-101, Amerchol) | 4.8 |
|   | Dimethicone | 1.6 |
|   | RTG Microfibrillar CMC as made in example 7 (DS about 0.16) | 0.6 |
| C | Lactic Acid (88%) | 0.3 |
|   | Germaben ® II (preservative) | 1.0 |

(As used herein, "anti-age" refers to that category of epidermal lotions and creams intended to contribute to a more youthful appearance by the user, such as by the reduction or removal of wrinkles.) Procedure: The ingredients for part A were combined and heated to 75° C. The part B ingredients, except RTG microfibrillar CMC, were then combined and heated to 75° C. until homogeneous. The RTG microfibrillar CMC was then dispersed into part B. Part B was next added to part A until the mixture became smooth and homogeneous. The mixture was then cooled to 40° C., and part C was added. This composition was formulated at pH 3.5–4.0, and stabilized with microfibrillar CMC rather than with typical xanthan, clay mixtures.

Properties

| | |
|---|---|
| pH | 3.7 |
| Viscosity* (cP) at 25° C. | 932,000 |
| Appearance | Glossy white, stiff cream |
| Stability | >5 weeks at 50° C. |

*Complex viscosity in linear viscoelastic regime was measured with a Bohlin rheometer.

This example demonstrates the ability of the RTG CMC material to stabilize an oil in water emulsion at low pH.

High SPF Organic Sunscreen Cream

| Phase | Ingredient | Wt % |
|---|---|---|
| A | DI water | 63.9 |
| B | Cetearyl Alcohol and Cetearyl Phosphate (Crodafos CES, Croda) | 6.6 |
| C | Benzophenone-3 | 5.0 |
|   | Octyl methoxycinnamate | 7.5 |
|   | Octyl Salicylate | 5.0 |
|   | Menthyl Anthranilate | 5.0 |
|   | Octyl Stearate | 5.0 |
| D | RTG Microfibrillar CMC as in example 7 (DS about 0.16) | 0.3 |
| E | NaOH, 18% | 0.6 |
| F | Butylated hydroxytoluene | 0.1 |
|   | Germaben ® II (preservative) | 1.0 |

Procedure: The ingredients for part A and part B were combined and heated to 70° C. Part C was then added separately, mixing after addition of each part C ingredient. Part D was then added with vigorous agitation, which was continued until the mixture became smooth and homogeneous. Part E was then added, the mixture was cooled to 45° C., and part F was added.

Properties

| | |
|---|---|
| pH | 5.9 |
| Viscosity* (cP) at 25° C. | 613,000 |
| Appearance | Light, off-white cream |
| Stability | >5 weeks at 50° C. |

*Complex viscosity in linear viscoelastic regime was measured with a Bohlin rheometer.

This example demonstrates use of microfibrillated CMC with organic sunscreen.

Formulation of a TiO$_2$ Based Sunscreen Lotion

| Phase | Ingredient | Wt % |
|---|---|---|
| A | DI water | 67.2 |
|   | Disodium ethylene diamine tetraacetic acid | 0.1 |
|   | Propylene Glycol | 5.0 |
| B | C$_{12-15}$ Alkyl Benzoate | 3.0 |
|   | Butyl Stearate | 3.0 |
|   | Myristyl Myristate | 4.0 |
|   | Sorbitan Oleate | 0.1 |
|   | RTG Microfibrillar CMC as in example 7 (DS about 0.16) | 0.6 |
| C | Germaben ® II (preservative) | 1.0 |
|   | Titanium Dioxide | 6.0 |
| D | Octyl Palmitate | 9.0 |
|   | Polyglyceryl-10 decaoleate | 1.0 |

Procedure: the ingredients for part A were combined and heated to 50° C. All of the part B ingredients, except microfibrillar CMC, were combined and heated to 60–65° C. until homogeneous. The microfibrillar CMC was then dispersed into part B, which was then added to part A with vigorous agitation, and agitation was continued until the mixture was smooth and homogeneous. The ingredients for part D were combined and mixed well. Part C was added to the AB emulsion; then, with moderate agitation, part D was slowly added to the emulsion and cooled to 30° C.

Properties

| | |
|---|---|
| pH | 7.1 |
| Viscosity* (cP) at 25° C. | 33,900 |
| Appearance | Glossy, white emulsion gel |
| Stability | >5 weeks at 50° C. |

*Complex viscosity in linear viscoelastic regime was measured with a Bohlin rheometer.

This example demonstrates use of microfibrillated CMC with inorganic sunscreen. The present invention has of necessity been discussed herein by reference to certain specific methods and materials. The enumeration of these methods and materials was merely illustrative, and in no way constitutes any limitation on the scope of the present invention. It is to be expected that those skilled in the art may discern and practice variations of or alternatives to the specific teachings provided herein, without departing from the scope of the present invention.

The present invention has of necessity been discussed herein by reference to certain specific methods and materials. The enumeration of these methods and materials was merely illustrative, and in no way constitutes any limitation on the scope of the present invention. It is to be expected that those skilled in the art may discern and practice variations of or alternatives to the specific teachings provided herein, without departing from the scope of the present invention.

We claim:

1. A derivatized microfibrillar polysaccharide, derivatized to comprise substituents that provide electrostatic and/or steric functionality, said electrostatic functionality comprising anionic charge, wherein the derivatized microfibrillar polysaccharide is characterized by forming a gel in water at at least one point in the concentration range of from about 0.05 wt. % to about 0.99 wt. % based on the total weight of the gel.

2. The derivatized microfibrillar polysaccharide of claim 1, wherein the polysaccharide in said derivatized microfibrillar polysaccharide comprises at least one of cellulose, hemicellulose, chitin, chitosan, guar gum, pectin, alginate, agar, xanthan, starch, amylose, amylopectin, alternan, gellan, mutan, dextran, pullulan, fructan, locust bean gum, carrageenan, glycogen, glycosaminoglycans, murein, bacterial capsular polysaccharides, and derivatives thereof.

3. The derivatized microfibrillar polysaccharide of claim 2, wherein said polysaccharide is at least one of cellulose, chitin, chitosan, pectin, agar, starch, carrageenan, and derivatives thereof.

4. The derivatized microfibrillar polysaccharide of claim 3, comprising derivatized microfibrillar cellulose.

5. The derivatized microfibrillar polysaccharide of claim 4, wherein said cellulose is obtained from at least one of chemical pulps, mechanical pulps, thermal mechanical pulps, chemical-thermal mechanical pulps, recycled fibers, newsprint, cotton, soybean hulls, pea hulls, corn hulls, flax, hemp, jute, ramie, kenaf, manila hemp, sisal hemp, bagasse, corn, wheat, bamboo, velonia, bacteria, algae, fungi, microcrystalline cellulose, vegetables, and fruits.

6. The derivatized microfibrillar polysaccharide of claim 5, wherein said cellulose is obtained from at least one of optionally bleached wood pulps produced from sulfite, kraft, or prehydrolyzed kraft pulping processes; cotton linters; fruits; and vegetables.

7. The derivatized microfibrillar cellulose of claim 4, comprising at least one of microfibrillated hydroxyethyl cellulose, microfibrillated ethylhydroxyethyl cellulose, microfibrillated carboxymethylcellulose, microfibrillated carboxymethylhydroxyethyl cellulose, microfibrillated hydroxypropylhydroxyethyl cellulose, microfibrillated methyl cellulose, microfibrillated methylhydroxypropyl cellulose, microfibrillated methylhydroxyethyl cellulose, microfibrillated carboxymethylmethyl cellulose, microfibrillated hydrophobically modified carboxymethylcellulose, microfibrillated hydrophobically modified hydroxyethyl cellulose, microfibrillated hydrophobically modified hydroxypropyl cellulose, microfibrillated hydrophobically modified ethylhydroxyethyl cellulose, microfibrillated hydrophobically modified carboxymethylhydroxyethyl cellulose, microfibrillated hydrophobically modified hydroxypropylhydroxyethyl cellulose, microfibrillated hydrophobically modified methyl cellulose, microfibrillated hydrophobically modified methylhydroxypropyl cellulose, microfibrillated hydrophobically modified methylhydroxyethyl cellulose, microfibrillated hydrophobically modified carboxymethylmethyl cellulose, microfibrillated nitrocellulose, microfibrillated cellulose acetate, microfibrillated cellulose sulfate, microfibrillated cellulose vinyl sulfate, microfibrillated cellulose phosphate, and microfibrillated cellulose phosphonate.

8. The derivatized microfibrillar cellulose of claim 4, wherein said derivatized microfibrillar cellulose forms a gel in water throughout the concentration range of between about 0.01 wt. % and about 100 wt. % solids based on the total weight of the gel.

9. The derivatized microfibrillar cellulose of claim 4, wherein said derivatized microfibrillar cellulose forms a gel in water throughout the concentration range of between about 0.01 wt. % and about 50 wt. % solids based on the total weight of the gel.

10. The derivatized microfibrillar cellulose of claim 4, wherein said derivatized microfibrillar cellulose forms a gel in water at at least one point in the concentration range of from about 0.05 wt. % up to about 0.99 wt. % solids based on the total weight of the gel.

11. The derivatized microfibrillar cellulose of claim 4, comprising carboxymethylcellulose.

12. The derivatized microfibrillar polysaccharide of claim 4, wherein said derivatized microfibrillar cellulose forms a gel in water at a concentration of less than about 1 wt. % solids based on the total weight of the gel.

13. The derivatized microfibrillar polysaccharide of claim 1, further comprising a solvent, wherein said derivatized microfibrillar polysaccharide is substantially insoluble in said solvent.

14. The derivatized microfibrillar polysaccharide of claim 13, wherein said solvent is water, alcohol, or oil.

15. The derivatized microfibrillar polysaccharide of claim 14, wherein said solvent is water.

16. The derivatized microfibrillar polysaccharide of claim 15, wherein said derivatized microfibrillar polysaccharide is derivatized to comprise substituents that provide electrostatic functionality.

17. The derivatized microfibrillar polysaccharide of claim 15, wherein said derivatized microfibrillar polysaccharide is derivatized to comprise substituents that provide steric functionality.

18. The derivatized microfibrillar polysaccharide of claim 17, having a molar substitution of less than about 3.0.

19. The derivatized microfibrillar polysaccharide of claim 18, wherein said molar substitution is less than about 1.5.

20. The derivatized microfibrillar polysaccharide of claim 19, wherein said molar substitution is less than about 1.0.

21. The derivatized microfibrillar polysaccharide of claim 20, wherein said molar substitution is less than about 0.5.

22. The derivatized microfibrillar polysaccharide of claim 18, wherein said molar substitution is between about 0.5 and 3.0.

23. The derivatized microfibrillar polysaccharide of claim 17, wherein said substituents comprise at least one of hydroxyethyl groups; hydroxypropyl groups; methyl groups; ethyl groups; straight- or branched-chain alkyl, alkenyl, or alkynyl groups having from about 4 to about 30 carbons; aryl, arylalkyl, arylalkenyl, cyclic, and herterocyclic hydrocarbons having from about 4 to about 30 carbons; or combinations thereof.

24. The derivatized microfibrillar polysaccharide of claim 23, further wherein said derivatized microfibrillar polysaccharide is a derivatized microfibrillar cellulose.

25. The derivatized microfibrillar cellulose of claim 24, wherein said microfibrillar cellulose is further derivatized to provide electrostatic functionality with a degree of substitution of less than about 0.35.

26. The derivatized microfibrillar cellulose of claim 25, wherein said degree of substitution is less than about 0.20.

27. The derivatized microfibrillar cellulose of claim 26, wherein said degree of substitution is between about 0.02 and about 0.2.

28. The derivatized microfibrillar cellulose of claim 27, wherein said degree of substitution is between about 0.10 and about 0.2.

29. The derivatized microfibrillar polysaccharide of claim 1, wherein said derivatized microfibrillar polysaccharide comprises electrostatically derivatized microfibrillar cellulose having a degree of substitution of less than about 0.5.

30. The derivatized microfibrillar polysaccharide of claim 29, wherein said degree of substitution is less than about 0.35.

31. The derivatized microfibrillar polysaccharide of claim 30, wherein said degree of substitution is less than about 0.2.

32. The derivatized microfibrillar polysaccharide of claim 31, wherein said degree of substitution is less than about 0.18.

33. The derivatized microfibrillar polysaccharide of claim 32, wherein said degree of substitution is less than about 0.1.

34. The derivatized microfibrillar polysaccharide of claim 29, wherein said degree of substitution is between about 0.02 and about 0.5.

35. The derivatized microfibrilliar polysaccharide of claim 34, wherein said degree of substitution is between about 0.05 and about 0.2.

36. The derivatized microfibrillar polysaccharide of claim 1, derivatized to comprise substituents that provide electrostatic functionality in the form of anionic charge, wherein the degree of substitution representing substituents that provide electrostatic functionality in the form of anionic charge is at least about 0.02.

37. The derivatized microfibrillar polysaccharide of claim 1, wherein said anionic charge is provided by carboxyl, sulfate, sulfonate, phosphonate, or phosphate groups, or combinations thereof.

38. Microfibrillar carboxymethylcellulose having a degree of substitution of between about 0.10 and about 0.20.

39. A paper composition comprising derivatized microfibrillar cellulose derivatized to comprise groups that provide electrostatic and/or steric functionality, further wherein said electrostatic functionality comprises the presence of anionic charge.

40. The paper composition of claim 39, wherein said derivatized microfibrillar cellulose is microfibrillar carboxymethylcellulose.

* * * * *